United States Patent
Thompson et al.

(10) Patent No.: US 9,527,872 B2
(45) Date of Patent: Dec. 27, 2016

(54) HYBRID ZEOLITIC IMIDAZOLATE FRAMEWORKS: CONTROLLING FRAMEWORK POROSITY AND FUNCTIONALITY BY A MIXED-LIGAND SYNTHETIC APPROACH

(71) Applicant: Georgia Tech Research Corporation, Atlanta, GA (US)

(72) Inventors: Joshua Allen Thompson, Atlanta, GA (US); Catherine Rose Blad, Atlanta, GA (US); Christopher W. Jones, Mableton, GA (US); Sankar Nair, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 568 days.

(21) Appl. No.: 13/754,430

(22) Filed: Jan. 30, 2013

(65) Prior Publication Data

US 2013/0197235 A1   Aug. 1, 2013

Related U.S. Application Data

(60) Provisional application No. 61/592,197, filed on Jan. 30, 2012.

(51) Int. Cl.

| | | |
|---|---|---|
| *C07F 3/06* | (2006.01) | |
| *B01D 53/02* | (2006.01) | |
| *C01B 37/00* | (2006.01) | |
| *C01B 39/00* | (2006.01) | |
| *C07F 3/00* | (2006.01) | |
| *B01J 20/22* | (2006.01) | |

(52) U.S. Cl.
CPC .............. *C07F 3/06* (2013.01); *B01D 53/02* (2013.01); *B01J 20/226* (2013.01); *C01B 37/00* (2013.01); *C01B 39/00* (2013.01); *C07F 3/003* (2013.01); *B01D 2253/204* (2013.01); *B01D 2257/504* (2013.01); *Y02C 10/08* (2013.01); *Y02P 20/152* (2015.11)

(58) Field of Classification Search
CPC .................................. C07F 3/06; B01J 20/226
See application file for complete search history.

(56) References Cited

PUBLICATIONS

Thompson et al. "Hybrid Zeolitic Imidazolate Frameworks: Controlling Framework Porosity and Functionality by Mixed-Linker Synthesis" Chemistry of Materials, 2012, vol. 24, pp. 1930-1936.*
Huang et al. "Steam-Stable Zeolitic Imidazolate Framework ZIF-90 Membrane with Hydrogen Selectivity through Covalent Functionalization" Journal of the American Chemical Society, 2010, vol. 132, pp. 15562-15564.*
Park et al. "Exceptional chemical and thermal stability of zeolitic imidazolate frameworks" PNAS, 1996, vol. 103, {ages 10186-10191.*
Zhang et al. "A hybrid zeolitic imidazolate framework membrane by mixed-linker synthesis for efficient CO2 capture" Chemical Communications, 2013, vol. 49, pp. 600-602.*

* cited by examiner

*Primary Examiner* — Joseph Kosack
(74) *Attorney, Agent, or Firm* — Troutman Sanders LLP; Ryan A. Schneider; Elizabeth-Ann Weeks

(57) ABSTRACT

Metal-organic frameworks, in particular hybrid zeolitic imidazolate frameworks (ZIFs), devices having hybrid ZIFs, and methods for preparing hybrid ZIFs are disclosed herein. In some embodiments, the method includes preparing a first solution comprising a first imidazolate and a second imidazolate, preparing a second solution comprising a metal ion, and combining the first solution and the second solution to form the hybrid ZIF.

17 Claims, 14 Drawing Sheets

HYBRID ZEOLITIC IMIDAZOLATE FRAMEWORKS: CONTROLLING FRAMEWORK POROSITY AND FUNCTIONALITY BY A MIXED-LIGAND SYNTHETIC APPROACH

CROSS-REFERENCE TO RELATED APPLICATIONS

This application claims the benefit of U.S. Provisional Application Ser. No. 61/592,197, filed on 30 Jan. 2012, entitled "Hybrid Zeolitic Imidazolate Frameworks: Controlling Framework Porosity and Functionality by a Mixed-Ligand Synthetic Approach," which is incorporated herein by reference in its entirety as if fully set forth below.

TECHNICAL FIELD

The various embodiments of the disclosure relate generally to zeolitic imidazolate frameworks (ZIF) and their associated fabrication processes, and more particularly to tunable, hybrid ZIFs and to methods for making such structures.

BACKGROUND

Framework modification of porous materials has considerable potential to enable tuning of material properties to increase performance in a variety of applications such as separations, catalysis, and chemical sensors. In particular, improving material performance for separations is highly desirable to reduce the overall process energy requirements. Typically, the two material properties in porous materials that determine separation performance are pore size (kinetic separation) and adsorption selectivity (thermodynamic effect). From this perspective, a nanoporous class of metal-organic frameworks (MOFs) called zeolitic imidazolate frameworks (ZIFs) are an attractive option.

MOFs are a promising class of nanoporous materials for use in separations and catalysis, among many other applications. ZIFs, a subclass of these materials, have many advantageous properties including good thermal and chemical stability, high microporosity, and high surface area. The pore sizes of these materials (0.2-2 nm) allow selective sieving and recognition of molecules. Recent studies have also shown that ZIFs exhibit a "gate-opening" phenomenon: as they interact with adsorbing molecules, they undergo structural changes during adsorption, thereby allowing more adsorbate molecules into the framework. Because the organic linker components in the framework rotate to allow the above phenomena, the nature of the organic linker has significant implications on the selection and behavior of appropriate ZIF materials for specific applications. For instance, ZIF-8 has a crystallographic pore aperture of 0.34 nm as determined by X-ray diffraction; however, there is increasing evidence that the as-made material separates gases considerably larger than its pore aperture (e.g., $C_3H_6$/$C_3H_8$) more efficiently than gases closer to its crystallographically determined pore size ($CO_2$/$CH_4$).

In general, it is possible to tune the properties of MOFs for specific applications using methods such as chemical or structural modifications. One approach for chemically modifying a MOF is to use a linker that has a pendant functional group for post-synthesis modification. For example, ZIF-90, an aldehyde-containing ZIF, can be modified using $NaBH_4$ as a reducing agent to generate alcohol groups. Another approach to modification is to use organic ligands that can change the structural characteristics of the material. MIL-53 exhibits a flexible framework, but modification of the terephthalic acid linker to include an amino functional group improves the separation performance for $CO_2$. Another recent approach to modification is the use of a triazolate linker in which a C—H moiety of the imidazole is replaced by a nitrogen atom, thereby allowing crystallization of a hybrid material that does not disturb the crystal structure of the original material. However, in the case of using mixed linkers, determining appropriate ligand combinations a priori is not always straightforward. It has been shown that the use of ligands with bulky substituents produces new ZIF frameworks with enhanced $CO_2$ adsorption properties by preventing crystallization of ZIF topologies with smaller unit cells and network cages; however, this discovery came from using high-throughput synthesis techniques. Similarly, the pore size of a MOF can be tuned by increasing the length of bridging organic linkers. A series of mixed-ligand Zn-based MOFs were transformed from a nonporous material to one with relatively high surface area and porosity by increasing the length of bridging dicarboxylic or bipyridyl linkers.

Another way to modify surface properties is by postsynthetic exchange (PSE) of the organic linkers or metal centers by heating the MOF material in a solvent containing a different linker or metal ion that exchanges into the material while maintaining the crystal structure. Recently, the linker of ZIF-71 (4,5-dichloroimidazole) was successfully subjected to PSE with a linker that is not otherwise found in ZIF structures (4-bromoimidazole). ZIF-8 has also been subjected to PSE, replacing the framework linkers (2-methylimidazole) with imidazole. This produced a material with 85% substituted linkers while maintaining the ZIF-8 crystal structure.

The different ZIF topologies can possess a variety of pore sizes and surface properties. ZIFs have been studied for $CO_2$ adsorption and membrane-based separations by both experiments and computations. Although these materials normally have high $CO_2$ capacity, the adsorption selectivity for typical gas pairs of interest (e.g., $CO_2$/$CH_4$) tends to be low and comparable with commercially available adsorbent materials such as BPL carbon. Practically, increasing the adsorption selectivity would greatly increase the potential for commercialization. Currently, very few ZIF materials (e.g., ZIF-78) have shown significant $CO_2$/$CH_4$ and $CO_2$/$N_2$ adsorption selectivities of 10 and 50, respectively, or more. Some large pore MOF structures exhibit higher $CO_2$ affinity and selectivity for these gas pairs; however, these materials typically have open metal centers that are susceptible to performance degradation from steam exposure and poison from trace contaminants, which adversely affect $CO_2$ capacity. Conversely, ZIFs have relatively high thermal and chemical stability that permits modification of the surface properties and have the added benefit of small pore apertures that are promising for kinetic gas separations, which further improves separation performance.

BRIEF SUMMARY

The various embodiments of the disclosure relate generally to zeolitic imidazolate frameworks (ZIF) and their associated fabrication processes, and more particularly to tunable, hybrid ZIFs and to methods for making such structures.

An embodiment of the disclosure can be a method for forming a hybrid zeolitic imidazolate framework (ZIF) having the steps of preparing a first solution comprising a first imidazolate and a second imidazolate, preparing a second solution comprising a metal ion, and combining the first solution and the second solution to form the hybrid ZIF. In one embodiment, the process can further comprise activating the hybrid ZIF to remove impurities. For example, the activating can comprise vacuum degassing between about 100° C. and about 300° C. In some embodiments, the first imidazolate is different from the second imidazolate. In one embodiment, the first imidazolate can comprise 2-methylimidazolate and the second imidazolate can comprise carboxaldehyde-2-imidazolate. In an alternative embodiment, the first imidazolate can comprise 2-methylimidazole and the second imidazolate can comprise benzimidazolate. In another embodiment, the first imidazolate can comprise benzimidazolate and the second imidazolate can comprise 2-aminobenzimidazolate. In yet another embodiment, the first imidazolate can comprise 2-methylimidazolate and the second imidazolate can comprise imidazolate.

The metal ion can comprise a transition metal. In one embodiment, the metal ion can comprise zinc. Alternatively, the metal ion can comprise cobalt.

In an embodiment, the method for forming a hybrid ZIF can further comprise functionalizing the hybrid ZIF. The functionalizing can comprise exposing the hybrid ZIF to a reactive agent. For example, the reactive agent can comprise an aldehyde. Alternatively, the reactive agent can comprise an amine.

An embodiment can be a metal-organic framework (MOF) that can comprise a hybrid ZIF comprising a first imidazolate, a second imidazolate, and a metal ion. In some embodiments, the first imidazolate is different from the second imidazolate. In one embodiment, the first imidazolate can comprise 2-methylimidazolate and the second imidazolate can comprise carboxaldehyde-2-imidazolate. In an alternative embodiment, the first imidazolate can comprise 2-methylimidazole and the second imidazolate can comprise benzimidazolate. In another embodiment, the first imidazolate can comprise benzimidazolate and the second imidazolate can comprise 2-aminobenzimidazolate. In yet another embodiment, the first imidazolate can comprise 2-methylimidazolate and the second imidazolate can comprise imidazolate.

The metal ion can comprise a transition metal. In one embodiment, the metal ion can comprise zinc. Alternatively, the metal ion can comprise cobalt.

In one embodiment, the ZIF can have a $CO_2/CH_4$ selectivity of at least 1.2 times greater than a non-hybrid ZIF. In another embodiment, the ZIF can have a $CO_2/CH_4$ selectivity of at least 1.5 times greater than a non-hybrid ZIF. In yet another embodiment, the ZIF can have a $CO_2/CH_4$ selectivity of at least 1.8 times greater than a non-hybrid ZIF. Alternatively, the ZIF can have a $CO_2/CH_4$ selectivity of at least 2 times greater than a non-hybrid ZIF.

In some embodiments, the hybrid ZIF can have $CO_2/CH_4$ adsorption selectivity from about 2.5 to about 13.1. In other embodiments, the hybrid ZIF can have $CO_2/CH_4$ adsorption selectivity of at least 10. In alternative embodiments, the hybrid ZIF can have $CO_2/CH_4$ adsorption selectivity of at least 12. In another embodiment, the hybrid ZIF can have $CO_2/CH_4$ adsorption selectivity of at least 14. In yet another embodiment, the hybrid ZIF can have $CO_2/CH_4$ adsorption selectivity of at least 15.

In an embodiment, the hybrid ZIF can have a pore size from about 0.25 to about 0.40 nm. In another embodiment, the hybrid ZIF can have a pore size less than about 0.40. In an alternative embodiment, the hybrid ZIF can have a pore size of at least 0.40. In an yet another embodiment, the hybrid ZIF can have a continuous crystal structure.

In another embodiment, the hybrid ZIF can further comprise a functionalized hybrid ZIF. The functionalized hybrid ZIF can comprise an aldehyde. Alternatively, the functionalized hybrid ZIF can comprise an amine.

Another embodiment of the disclosure can be a molecular sieve device that can comprise a metal-organic framework (MOF) comprising a hybrid ZIF that can comprise a first imidazolate, a second imidazolate, and a metal ion. In some embodiments, the first imidazolate is different from the second imidazolate. In one embodiment, the first imidazolate can comprise 2-methylimidazolate and the second imidazolate can comprise carboxaldehyde-2-imidazolate. In an alternative embodiment, the first imidazolate can comprise 2-methylimidazole and the second imidazolate can comprise benzimidazolate. In another embodiment, the first imidazolate can comprise benzimidazolate and the second imidazolate can comprise 2-aminobenzimidazolate. In yet another embodiment, the first imidazolate can comprise 2-methylimidazolate and the second imidazolate can comprise imidazolate.

The metal ion can comprise a transition metal. In one embodiment, the metal ion can comprise zinc. Alternatively, the metal ion can comprise cobalt.

In one embodiment, the ZIF can have a $CO_2/CH_4$ selectivity of at least 1.2 times greater than a non-hybrid ZIF. In another embodiment, the ZIF can have a $CO_2/CH_4$ selectivity of at least 1.5 times greater than a non-hybrid ZIF. In yet another embodiment, the ZIF can have a $CO_2/CH_4$ selectivity of at least 1.8 times greater than a non-hybrid ZIF. Alternatively, the ZIF can have a $CO_2/CH_4$ selectivity of at least 2 times greater than a non-hybrid ZIF.

In some embodiments, the hybrid ZIF can have $CO_2/CH_4$ adsorption selectivity from about 2.5 to about 13.1. In other embodiments, the hybrid ZIF can have $CO_2/CH_4$ adsorption selectivity of at least 10. In alternative embodiments, the hybrid ZIF can have $CO_2/CH_4$ adsorption selectivity of at least 12. In another embodiment, the hybrid ZIF can have $CO_2/CH_4$ adsorption selectivity of at least 14. In yet another embodiment, the hybrid ZIF can have $CO_2/CH_4$ adsorption selectivity of at least 15.

In an embodiment, the hybrid ZIF can have a pore size from about 0.25 to about 0.40 nm. In another embodiment, the hybrid ZIF can have a pore size less than about 0.40. In an alternative embodiment, the hybrid ZIF can have a pore size of at least 0.40. In an yet another embodiment, the hybrid ZIF can have a continuous crystal structure.

In an alternative embodiment, the hybrid ZIF can further comprise a functionalized hybrid ZIF. The functionalized hybrid ZIF can comprise an aldehyde. Alternatively, the functionalized hybrid ZIF can comprise an amine.

DETAILED DESCRIPTION

Figure 1:
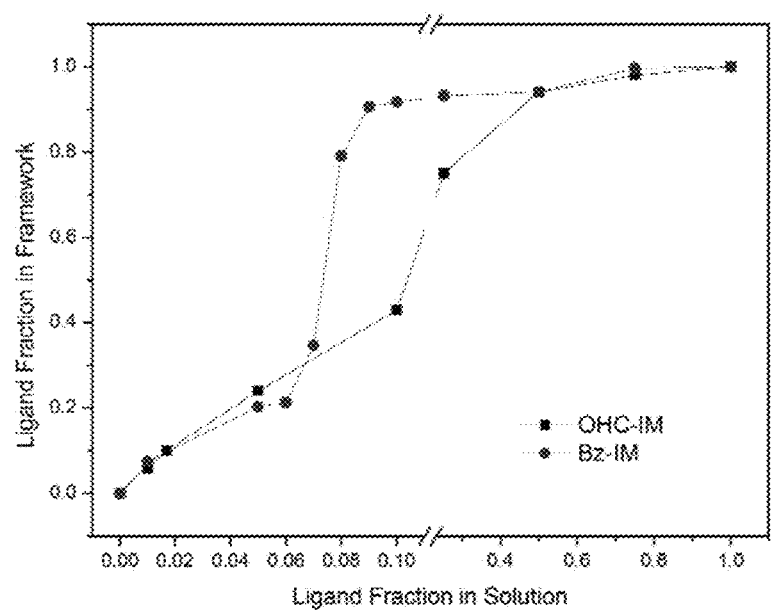
FIG. 1 illustrates compositional analysis of ZIF hybrid frameworks by $^1$H NMR, in accordance with an embodiment of the disclosure.

Although many embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, another embodiment includes from the one particular value and/or to the other particular value.

By "comprising" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Various embodiments of the disclosure are directed to zeolitic imidazolate frameworks (ZIF) and their associated fabrication processes, and more particularly to tunable, hybrid ZIFs and to methods for making such structures. A novel structural modification approach towards tuning the properties of ZIF materials is disclosed. In particular, hybrid ZIFs containing a combination of different ligands in differing relative quantities can be synthesized according to the present disclosure.

One particular advantage of this disclosure is the ability to manufacture continuously tunable framework functionality or microporosity. A further advantage is the ability to produce homogenous crystal structure frameworks that would normally form varying crystal structures. The present disclosure can improve upon the non-hybrid ZIFs. For example, characterization by X-ray diffraction and nitrogen physisorption demonstrates the formation of a set of crystalline ZIF structures that can exhibit adsorption properties different from their parent frameworks. Additionally, continuous control over composition can be possible, as shown by $^1$H NMR spectroscopy. Furthermore, the present disclosure relates to a method that can be a facile route whereby chemically and thermally robust ZIFs can be subjected to continuous and tunable alterations in chemical functionality or microporosity by in situ incorporation of various linkers, including various imidazoles, including imidazole and benzimidazole derivatives.

By the method disclosed herein, the surface functionalities in ZIF materials can be better controlled and improvement in gas separations can be realized without severely altering the pore volume of the material. Additionally, by the methods of the present disclosure, in situ linker substitution can be performed in various MOFs, including ZIFs, with two different linkers to introduce two different functionalities in the material without changing the crystal structure. For example, 2-aminobenzimidazole, a linker not found in other ZIF materials, can be incorporated into the ZIF-8 structure, with good control over the linker substitution stoichiometry. Although this linker contains a primary amine functional group, it can have little effect on the $CO_2$ adsorption affinity even at high substitution loadings. Without wishing to be bound by theory, it is thought that the reduced effect on the $CO_2$ adsorption affinity can be due to the aromaticity of the linker which reduces the basicity of the primary amine.

Various MOFs can be manufactured using the methods of this disclosure including, but not limited to mixed-linker ZIFs that can undergo post-synthetic modification (PSM) without detrimental loss of pore volume. Furthermore, ZIF materials can be produced that have high gas adsorption selectivities including, but not limited to, $CO_2/CH_4$ adsorption selectivity.

An embodiment of the disclosure can be a method for forming a hybrid zeolitic imidazolate framework (ZIF) comprising the steps of preparing a first solution comprising a first imidazolate and a second imidazolate, preparing a second solution comprising a metal ion, and combining the first solution and the second solution to form the hybrid ZIF. In one embodiment, the process can further comprise activating the hybrid ZIF to remove impurities. In some embodiments, the first imidazolate is different from the second imidazolate. In one embodiment, the first imidazolate can comprise 2-methylimidazolate and the second imidazolate can comprise carboxaldehyde-2-imidazolate. In an alternative embodiment, the first imidazolate can comprise 2-methylimidazole and the second imidazolate can comprise benzimidazolate. In another embodiment, the first imidazolate can comprise benzimidazolate and the second imidazolate can comprise 2-aminobenzimidazolate. In yet another embodiment, the first imidazolate can comprise 2-methylimidazolate and the second imidazolate can comprise imidazolate. In some embodiments, the first imidazolate can comprise 2-methylimidazolate or benzimidazolate. In other embodiments, the second imidazolate can comprise benzimidazolate, 2-aminoimidazolate, imidazolate, or carboxaldehyde-2-imidazolate. Alternatively, one of ordinary skill in the art would recognize that a variety of imidazolate linkers with different functionalities can be used to form the hybrid ZIFs, including imidazolate derivatives and benzimidazolate derivatives. The functionalities can be the first imidazolate or the second imidazolate. The various functionalities can include, but are not limited to alkyl, amino, chloro, bromo, carbonyl, nitro, sulfonate, hydroxy, hydroxo, aldehyde, organometallic functionalities, and the like.

The metal ion can comprise a transition metal. For example, the metal ion can comprise a first row transition metal such as nickel, iron, zinc, or cobalt. In some embodiments, the metal ion can comprise zinc or cobalt. In one embodiment, the metal ion can comprise zinc. Alternatively, the metal ion can comprise cobalt.

The activating can remove species such as solvent, unreacted metal ions or unreacted imidazolate remaining in the pore of the ZIF. The activating can comprise any ZIF activating process commonly known in the art, including but not limited to, heat treating, vacuum degassing. For example, the activating can comprise vacuum degassing between about 100° C. and about 300° C.

In an embodiment, the method for forming a hybrid ZIF can further comprise functionalizing the hybrid ZIF. The functionalizing can comprise exposing the hybrid ZIF to a reactive agent. A reactive agent can be any reagent known in the art that can undergo a chemical reaction with the hybrid ZIF. For example, the reactive agent can comprise an aldehyde. Alternatively, the reactive agent can comprise an amine. In one embodiment, the reactive agent cam comprise an aldehyde or an amine.

An embodiment can be a metal-organic framework (MOF) that can comprise a hybrid ZIF comprising a first imidazolate, a second imidazolate, and a metal ion. In some embodiments, the first imidazolate is different from the second imidazolate. In one embodiment, the first imidazolate can comprise 2-methylimidazolate and the second imidazolate can comprise carboxaldehyde-2-imidazolate. In an alternative embodiment, the first imidazolate can comprise 2-methylimidazole and the second imidazolate can comprise benzimidazolate. In another embodiment, the first imidazolate can comprise benzimidazolate and the second imidazolate can comprise 2-aminobenzimidazolate. In yet another embodiment, the first imidazolate can comprise 2-methylimidazolate and the second imidazolate can comprise imidazolate.

The metal ion can comprise a transition metal. In one embodiment, the metal ion can comprise zinc. Alternatively, the metal ion can comprise cobalt.

The hybrid ZIF of the present disclosure can have an increased selectivity for many gas pairs as compared to a non-hybrid ZIF. Without wishing to be bound by theory, it is thought that better selectivity can be derived from either a change in pore size of the hybrid ZIF materials, or a change in surface properties by introducing organic functional groups into the framework. Having a smaller pore size can result in better diffusion selectivity for small gas pairs while changing the organic functional groups can increase the adsorption selectivity. By way of non-limiting examples, the hybrid ZIF can have a greater selectivity for the following gas pairs: $CO_2/CH_4$, $CO_2/N_2$, $O_2/N_2$, $C_2H_4/C_2H_6$, $C_3H_6/C_3H_8$, and the like. In one embodiment, the hybrid ZIF can have a $CO_2/CH_4$ selectivity of at least 1.2 times greater than a non-hybrid ZIF. In another embodiment, the ZIF can have a $CO_2/CH_4$ selectivity of at least 1.5 times greater than a non-hybrid ZIF. In yet another embodiment, the ZIF can have a $CO_2/CH_4$ selectivity of at least 1.8 times greater than a non-hybrid ZIF. Alternatively, the ZIF can have a $CO_2/CH_4$ selectivity of at least 2 times greater than a non-hybrid ZIF.

In some embodiments, the hybrid ZIF can have $CO_2/CH_4$ adsorption selectivity from about 2.5 to about 13.1. In other embodiments, the hybrid ZIF can have $CO_2/CH_4$ adsorption selectivity of at least 10. In alternative embodiments, the hybrid ZIF can have $CO_2/CH_4$ adsorption selectivity of at least 12. In another embodiment, the hybrid ZIF can have $CO_2/CH_4$ adsorption selectivity of at least 14. In yet another embodiment, the hybrid ZIF can have $CO_2/CH_4$ adsorption selectivity of at least 15. In still another embodiment, the hybrid ZIF can have a $CO_2/CH_3$ adsorption selectivity of at least 20. The present disclosure refers to adsorption selectivity; however, one of ordinary skill in the art to which this disclosure pertains would understand that there can also be a difference or increase in diffusion selectivity also.

By the present disclosure, hybrid ZIFs can be manufactured that have reduced pore volumes compared with their counterpart non-hybrid ZIFs. Reduced poor sizes can lead to better kinetic separation performance using pure hybrid ZIF membranes and/or hybrid ZIF composite membranes. Furthermore, the reduction in the average pore size of the hybrid ZIF can enable the control of the gate-opening phenomena observed in the interaction of ZIF materials with molecules such as $N_2$ and $O_2$. In an embodiment, the hybrid ZIF can have a pore size from about 0.25 to about 0.40 nm. In another embodiment, the hybrid ZIF can have a pore size less than about 0.40. In an alternative embodiment, the hybrid ZIF can have a pore size of at least 0.40.

In an alternative embodiment, the hybrid ZIF can have a continuous crystal structure. It has been unexpectedly found that in the present disclosure, the crystal structure can be near-identical to a non-hybrid ZIF in terms of the arrangement of metal ions and the linkers. A non-hybrid ZIF is herein defined as a ZIF comprising only one imidazolate linker. Typically, only one structure can be obtained when synthesizing a ZIF with one particular organic linker. For example, the only structure observed with 2-methylimidazole as the linker is ZIF-8. It can be possible to manufacture a ZIF with a mixture of linkers, but this can require specific amounts of each linker. A hybrid ZIF, in this case, can be a material that can be synthesized with a different linker composition from the original crystal structure and the linker composition can be tunable by changing the ratios of the linkers in the composition. Maintenance of the overall crystal structure can be advantageous because it can allow for the creation of a continuously tunable met of materials starting from a 'baseline' ZIF that can be thermally and chemically stable, but each member of the set can exhibit different in applicability to a range of separations. It would be clear to one of ordinary skill in the art that the identity of the linkers can change depending on the extent of hybridization.

In one embodiment, the hybrid ZIF can further comprise a functionalized hybrid ZIF. The functionalized hybrid ZIF can comprise an aldehyde. Alternatively, the functionalized hybrid ZIF can comprise an amine.

Another embodiment of the disclosure can be a molecular sieve device that can comprise a metal-organic framework (MOF) comprising a hybrid ZIF that can comprise a first imidazolate, a second imidazolate, and a metal ion. In some embodiments, the first imidazolate is different from the second imidazolate. In one embodiment, the first imidazolate can comprise 2-methylimidazolate and the second imidazolate can comprise carboxaldehyde-2-imidazolate. In an alternative embodiment, the first imidazolate can comprise 2-methylimidazolate and the second imidazolate can comprise benzimidazolate. In another embodiment, the first imidazolate can comprise benzimidazolate and the second imidazolate can comprise 2-aminobenzimidazolate. In yet another embodiment, the first imidazolate can comprise 2-methylimidazolate and the second imidazolate can comprise imidazolate.

The metal ion can comprise a transition metal. In one embodiment, the metal ion can comprise zinc. Alternatively, the metal ion can comprise cobalt.

In one embodiment, the ZIF can have a $CO_2/CH_4$ selectivity of at least 1.2 times greater than a non-hybrid ZIF. In another embodiment, the ZIF can have a $CO_2/CH_4$ selectivity of at least 1.5 times greater than a non-hybrid ZIF. In yet another embodiment, the ZIF can have a $CO_2/CH_4$ selectivity of at least 1.8 times greater than a non-hybrid ZIF. Alternatively, the ZIF can have a $CO_2/CH_4$ selectivity of at least 2 times greater than a non-hybrid ZIF.

In some embodiments, the hybrid ZIF can have $CO_2/CH_4$ adsorption selectivity from about 2.5 to about 13.1. In other embodiments, the hybrid ZIF can have $CO_2/CH_4$ adsorption selectivity of at least 10. In alternative embodiments, the hybrid ZIF can have $CO_2/CH_4$ adsorption selectivity of at least 12. In another embodiment, the hybrid ZIF can have $CO_2/CH_4$ adsorption selectivity of at least 14. In yet another embodiment, the hybrid ZIF can have $CO_2/CH_4$ adsorption selectivity of at least 15.

In an embodiment, the hybrid ZIF can have a pore size from about 0.25 to about 0.40 nm. In another embodiment, the hybrid ZIF can have a pore size less than about 0.40. In an alternative embodiment, the hybrid ZIF can have a pore size of at least 0.40. In an yet another embodiment, the hybrid ZIF can have a continuous crystal structure.

In an embodiment, the hybrid ZIF can further comprise a functionalized hybrid ZIF. The functionalized hybrid ZIF can comprise an aldehyde. Alternatively, the functionalized hybrid ZIF can comprise an amine.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Example 1

Materials

Sodium formate (99%, $NaCO_2H$), 2-methylimidazole (99%, 2-MeIM), $Zn(NO_3)_2 \cdot 6H_2O$ (99%) and benzimidazole (99%, Bz-IM) were obtained from Sigma-Aldrich. Methanol (MeOH), dimethylformamide (DMF), and carboxaldehyde-2-imidazole (99%, OHC-IM) were obtained from Alfa Aesar. All materials were used without any further purification.

Synthesis of ZIF-8-90 Hybrids.

A solution of 20 mmol $NaCO_2H$, (20-x) mmol 2-MeIM (ZIF-8 linker) and x mmol OHC-IM (ZIF-90 linker) in 50 mL MeOH was prepared. The value x varied between 0-20 to alter the ratio of OHC-IM:2-MeIM in solution. In order to fully dissolve the OHC-IM ligand, the solution was heated to 50° C. until it became clear. A separate solution was prepared with 5 mmol $Zn(NO_3)_2.6H_2O$ and 50 mL deionized $H_2O$. After the MeOH solution cooled to room temperature, the Zn salt solution was poured into the 1M solution and allowed to stir at room temperature for 1 hr. The resulting milky solution was centrifuged at 10000 rpm for 5 min, and the precipitate was redispersed in 45 mL MeOH and washed three times. The powder was dried in an oven at 85° C.

Synthesis of ZIF-7-8 Hybrids.

A solution of 20 mmol $NaCO_2H$, (20-x) mmol 2-MeIM and x mmol of Bz-IM (ZIF-7 linker) in 50 mL MeOH was prepared. Like the ZIF-8-90 hybrids, the value x was changed to alter the Bz-IM:2-MeIM ratio. A separate solution was prepared with 5 mmol $Zn(NO_3)_2.6H_2O$ and 50 mL DMF. The Zn salt solution was poured into the 1M solution and allowed to stir at room temperature. Times for crystal formation varied between 1-48 hrs. The resulting suspension was centrifuged at 10000 rpm for 10 min, and the precipitate was redispersed in 45 mL MeOH. The product was washed three times and then recovered by vacuum filtration and dried in an oven at 85° C.

Characterization Methods.

Powder X-ray diffraction (XRD) was performed at room temperature on an X'Pert Pro PANalytical X-Ray Diffractometer using Cu Kα radiation of wavelength λ=1.5406 Å. Measurements were carried out from 4-50° 2θ, using an X'celerator detector with low background sample holders. For unit cell volume calculations in the ZIF-8-90 system, an internal standard (α-$Al_2O_3$) was added to the powder samples, and the diffraction pattern was shifted appropriately (typically by about 0.1° 2θ) such that the peak positions of the internal standard were correctly reproduced. Structureless (Le Bail) refinement of the full XRD patterns (excluding the internal standard peaks) was carried out with the Expo2009 package, to obtain a highly accurate cubic lattice constant (a) and hence the unit cell volume ($a^3$). Thermogravimetric and decomposition analyses were performed on a Netzsch STA-409-PG thermogravimetric analyzer (TGA) and differential scanning calorimeter (DSC). Powder samples were heated from room temperature to 900° C. with a ramp rate of 10 K/min in a diluted air stream (40% air-60% nitrogen). Smoothed differential mass loss curves were analyzed to determine decomposition temperature of hybrid materials. Solution $^1H$ NMR measurements were performed using a Mercury Vx 400 MHz spectrometer by digesting crystals using d4-acetic acid ($CD_3CO_2D$) as the solvent. To determine the fraction of imidazole linkers in the framework of each sample, the areas of each peak were normalized to either the aldehyde proton of OHC-1M (9.84 ppm) or the 2 position proton of Bz-IM (9.05 ppm). Particle size and morphology were examined using a JEOL 100CX transmission electron microscope (TEM) operating at 100 keV. Samples were dispersed in isopropanol and a drop of the dispersion was added to the TEM grid. Nitrogen physisorption measurements were carried out at 77 K on a Micromeritics ASAP 2020 surface area analyzer. Samples were first degassed for 18 hrs at 200° C. (ZIF-8-90 hybrids) or 250° C. (ZIF-7-8 hybrids) to remove occluded solvent molecules ($H_2O$ or DMF). Horváth-Kawazoe (HK) equations were used to analyze nitrogen physisorption isotherms of hybrid materials. The BET, Langmuir and t-plot micropore volume methods were used to analyze the relative surface properties of the hybrids.

Crystallization.

In preparing ZIF hybrids, some observations can be made about the behavior of the induction period and crystallization process. In all syntheses described here, the non-solvent induced crystallization (NSIC) technique was used. By introducing a non-solvent, rapid crystallization can occur due to a drastic solubility change in the reaction solution, and there can be a significant reduction (or elimination) of the induction period that involves precursor formation and crystallite nucleation. Because ZIF-8 has been synthesized in both non-solvents used in this study, we hypothesized that addition of $NaCO_2H$ to the reactants would increase the nucleation time due to competitive coordination with the $Zn^{2+}$ metal center. Furthermore, by using $NaCO_2H$ and the linkers in equimolar amounts, both linkers included in the framework can likely be largely deprotonated before addition of the Zn salt solution, thereby allowing for a more random distribution of linkers. Otherwise, deprotonation of the linker is driven by the energy of formation of the framework, and thus the ZIF with the more favorable lattice energy is more likely to crystallize in pure form rather than a phase containing a random mixture of linkers.

Upon adding the Zn salt solution in the ZIF-8-90 hybrid case, the solution remained clear for 30-60 s. A crystal suspension then formed rapidly. Crystal yields were 20-25% based on the fraction of added Zn incorporated into the crystals. ZIF-7-8 hybrids behaved quite differently during crystallization. Several solvent systems were employed, but only the DMF-MeOH solvent system yielded crystalline materials over a wide range of Bz-IM:2-MeIM ratios reported here. Upon adding the Zn-DMF solution, a long induction period of 1-4 hrs was observed in the case of low Bz-IM percentages (0-10%). Thus, these reactions were all carried out for 48 hrs at room temperature. However, at 25% Bz-IM, there was rapid crystal formation, and hence reactions with higher Bz-IM percentages were only carried out for 1 hr. Yields varied considerably with the percentage of Bz-IM used, with 10% Bz-IM having the lowest (~1% based on Zn) and 100% Bz-IM having the highest crystallization yield (67% yield based on Zn).

Composition Analysis.

$^1H$ NMR was used to quantify the fraction of substituting linker (Bz-IM or OHC-IM relative to 2-MeIM) in the crystals. Because the NSIC technique was used to form the hybrid materials, it can be expected that the linker with the lower solubility in the non-solvent can be incorporated in precursors to a larger extent than the other linker. FIG. 1 shows the fraction of substituting linker used in the reactant solution versus the corresponding fraction that resulted in the framework, as determined by $^1H$ NMR. Both OHC-IM and Bz-IM are incorporated into the framework at higher fractions than they are present in solution. It has been shown that ZIF-8 crystals grow in methanol solutions at room temperature by a nucleation-limited mechanism without addition of another coordinating linker. Considering that nucleation is further slowed by additives in the solution ($NaCO_2H$), it is likely that the OHC-IM and Bz-IM linkers are incorporated into nuclei precursors more favorably than the 2-MeIM linker due to the rapid solubility change by addition of the non-solvent during synthesis. The hybrid composition can clearly be controlled; however in the case of ZIF-7-8 hybrids, a precise control of the synthesis can be necessary to reach any arbitrary linker composition.

Crystal Structure.

Figure 2A:
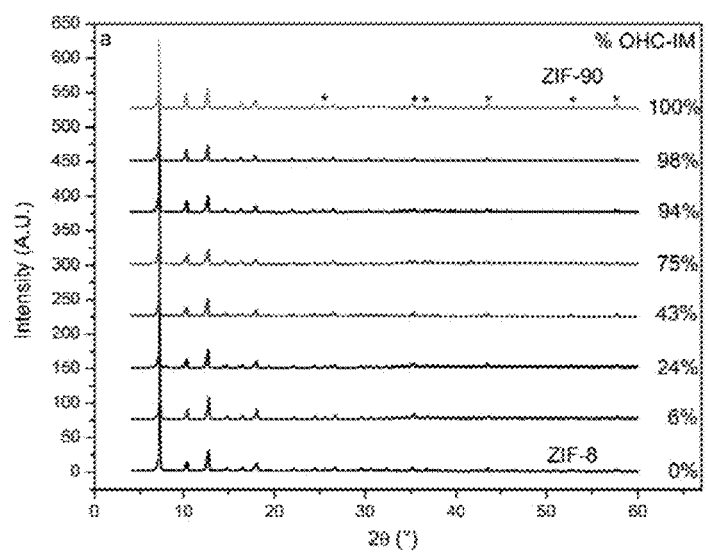
FIG. 2a illustrates powder XRD patterns of ZIF-8-90 hybrids, in accordance with an embodiment of the disclosure.
Figure 2B:
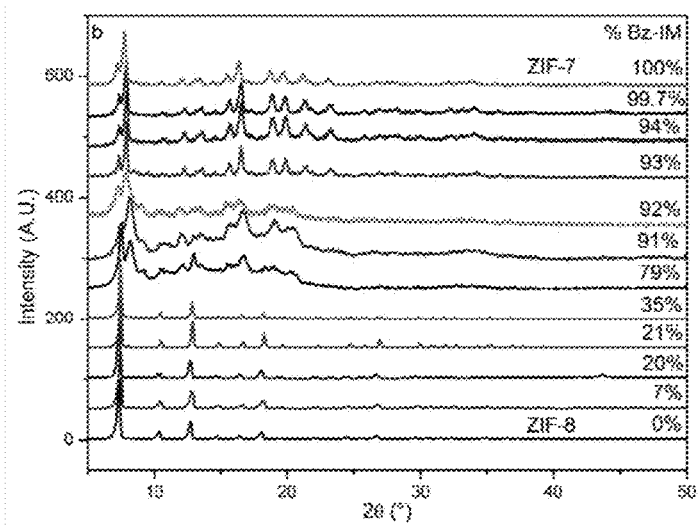
FIG. 2b illustrates powder XRD patterns of ZIF-7-8 hybrids, in accordance with an embodiment of the disclosure.

FIGS. 2a 1 and 2b show XRD patterns of the ZIF-8-90 and ZIF-7-8 hybrids, respectively. ZIF-8 and ZIF-90 have nearly identical I-43m cubic unit cells; structure refinement has shown that the unit cell dimension differs by 2-3%. This makes the XRD identification of separate phases during hybrid crystallization difficult. We obtained the unit cell volumes of the ZIF-8-90 hybrids using the Le Bail refinement technique. To account for peak position errors when measuring powder XRD patterns, the patterns were corrected using an $\alpha$-$Al_2O_3$ internal standard. There is an overall systematic increase in the unit cell volume with increasing OHC-IM fraction. This volume changes by 2.7% as the hybrid composition goes from pure ZIF-8 to pure ZIF-90.

On the other hand, ZIF-7 and ZIF-8 have considerably different crystal structures. Based on refinement, ZIF-7 has a rhombohedral R-3 space group while ZIF-8 has the cubic I-43m space group. Differences in XRD patterns are therefore easily discernible (FIG. 2b). Up to 35% Bz-IM loading, the framework still maintains a cubic structure characteristic of ZIF-8, and thereafter transitions to the R-3 space group. Between 79-92% Bz-IM, significantly disordered materials are obtained. The diffraction pattern of 79% Bz-IM, in particular, has an apparent superposition of both ZIF-8 and ZIF-7 phases; however, our subsequent TEM images show clearly that a physical two-phase mixture of ZIF-7 and ZIF-8 crystals does not exist. Because these materials have considerably different crystal structures, there can be compositional ranges wherein a hybrid with a completely random distribution of linkers is unable to crystallize. Therefore, this XRD pattern can represent an intergrowth of ZIF-7 and ZIF-8 phases. However, distinguishing an intergrown hybrid material from a hybrid that has a truly random linker distribution would require a detailed microcrystallographic study (e.g., with electron diffraction) and the development of suitable intergrowth models. For example, we attempted to perform an indexing of the three XRD patterns mentioned above; however, the number of distinct usable peaks is only about 10 and therefore a reliable and unambiguous indexing was not possible to address the question of whether or not an intergrown material was formed. No XRD patterns are shown for hybrids between loadings of 35-79% Bz-IM because of the narrow synthesis range (7-8% Bz-IM in solution) needed to obtain these materials. It is presently unclear whether hybrids in this composition range can be successfully obtained by a highly accurate adjustment of the reactant composition, or whether the materials in this range are unstable and hence transform to one of the phases obtained at lower or higher Bz-IM loadings. Further modification of the procedure could yield a material with a better range of tunability by producing more favorable crystallization conditions for the ZIF-7-8 hybrids. The XRD patterns shown, and the following TEM and nitrogen physisorption data, do not indicate the formation of a simple physical mixture of ZIF-7 and ZIF-8; instead, a single crystalline phase forms in every case.

Particle Size and Morphology.

Figure 3:
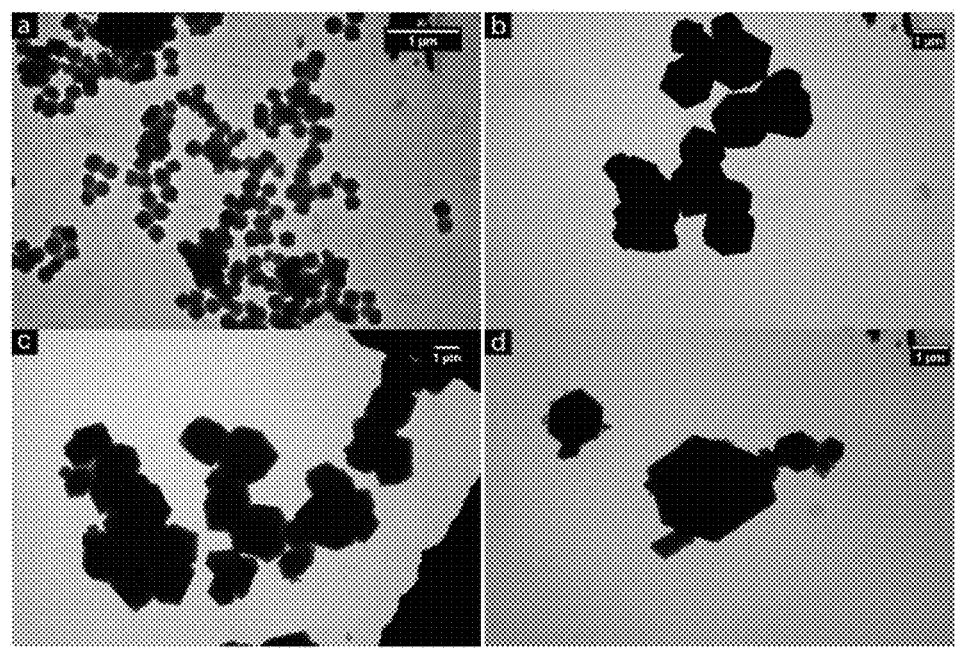
FIG. 3 illustrates TEM images of ZIF-8-90 hybrids at (a) 0%; (b) 24%; (c) 43%; and (d) 100% OHC-IM loading, in accordance with an embodiment of the disclosure.
Figure 4:
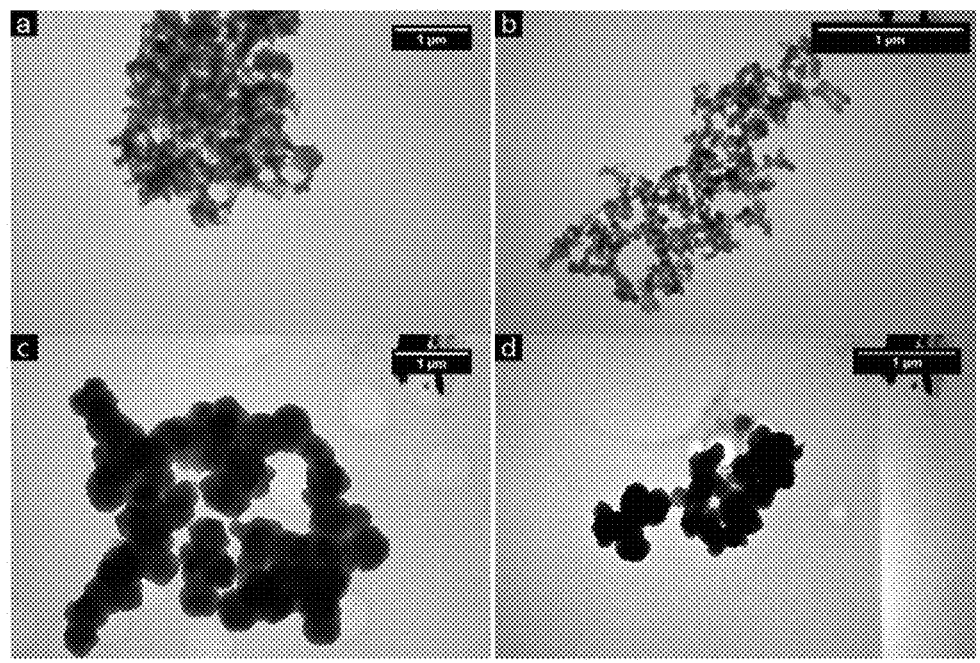
FIG. 4 illustrates TEM images of ZIF-7-8 hybrids at (a) 35%; (b) 91%; (c) 94%; and (d) 100% Bz-IM loading, in accordance with an embodiment of the disclosure.

TEM was used to examine changes in particle size or morphology with the linker composition. FIG. 3 shows TEM images of ZIF-8-90 hybrids at different OHC-IM loadings. At 0% OHC-IM (pure ZIF-8), particles show a monodisperse distribution centered at approximately 250 nm, exhibiting the typical rhombic dodecahedral morphology of ZIF-8 particles when synthesized with $NaCO_2H$. As the OHC-IM loading increases, the particle size increases, growing to more than 1 μm at 24% OHC-IM. Significantly, all the TEM images showed only one particle population and thereby suggest formation of a single-phase hybrid material. If ZIF-8 and ZIF-90 had precipitated separate phases, the particle sizes would likely be considerably different, since the pure ZIF-8 phase (FIG. 3a) exhibits sub-micron particles while the pure ZIF-90 phase (FIG. 3d) exhibits micron-sized particles. TEM images of ZIF-7-8 hybrids are shown in FIG. 4. The particle morphology of these materials is less well-defined than in the ZIF-8-90 hybrids, being closer to spherical in most cases than the rhombic dodecahedral morphology. This observation can support the formation of a single crystal phase different from both ZIF-7 and ZIF-8 at the intermediate loadings of Bz-IM, considering that ZIF-7 has been shown to form spherical or rod-like morphologies and ZIF-8 forms the rhombic dodecahedral morphology in the presence of an additive. The particle size of the disordered hybrid material shown in FIG. 4b is considerably smaller than that of the other materials in FIG. 4. As 2-MeIM is still the major organic linker in the solution, it can be preventing crystallization of the R-3 phase and resulting in low crystallization yields and the disordered rhombohedral-like structure shown by XRD Like the ZIF-8-90 hybrids, there are not different particle size populations or morphologies that indicate a physical mixture of the two phases.

Thermal Decomposition.

Figure 5A:
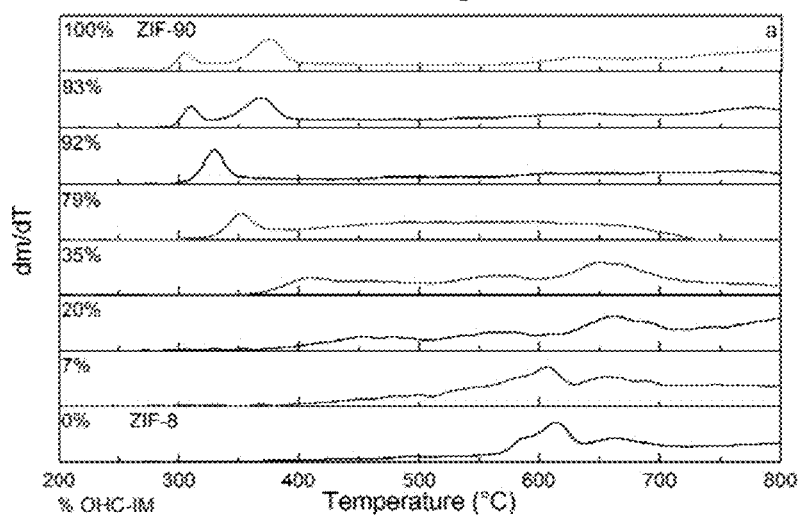
FIG. 5a illustrates differential mass loss curves of ZIF-8-90 as determined from thermogravimetry in a 40% air-60% nitrogen gas stream, in accordance with an embodiment of the disclosure.
Figure 5B:
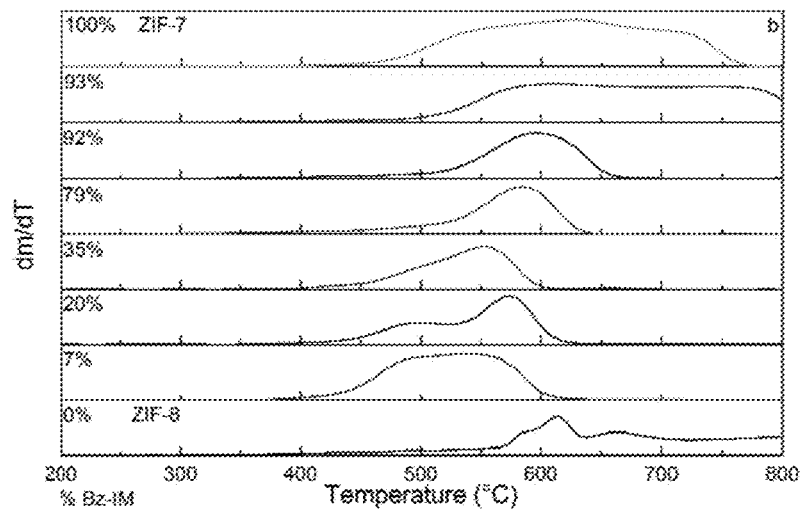
FIG. 5b illustrates differential mass loss curves of ZIF-7-8 hybrids as determined from thermogravimetry in a 40% air-60% nitrogen gas stream, in accordance with an embodiment of the disclosure.

Previous studies on thermal decomposition of ZIFs showed the existence of a wide range of decomposition temperatures that also depend on synthesis conditions. Thermogravimetric analysis (TGA) was used here to elucidate stability changes in the hybrid materials. To minimize the influence of solvent mass loss, samples were first degassed under vacuum for 12 hours at either 200° C. (ZIF-8-90) or 250° C. (ZIF-7-8). FIGS. 5a and 5b show differential mass loss curves for ZIF-8-90 and ZIF-7-8, respectively. ZIF-8 (0% OHC-IM) shows the highest thermal stability for the ZIF-8-90 hybrids, with nearly no decomposition observed until 450° C. At 24% OHC-IM loading, decomposition begins closer to 400° C., and above 50% OHC-IM loading, the hybrid frameworks are thermally stable up to 300° C. Aldehydes typically oxidize easily in air, and this is the likely cause of the lower thermal stability under exposure to diluted air at elevated temperatures. On the other hand, the onset of decomposition in ZIF-7-8 hybrids remains unchanged at 400-450° C. Materials at high loadings of Bz-IM (79-100%) are stable above 500° C. This increase in decomposition temperature of the framework can be attributed to the greater stability provided by the aryl groups of Bz-IM.

Porosity.

Figure 6A:
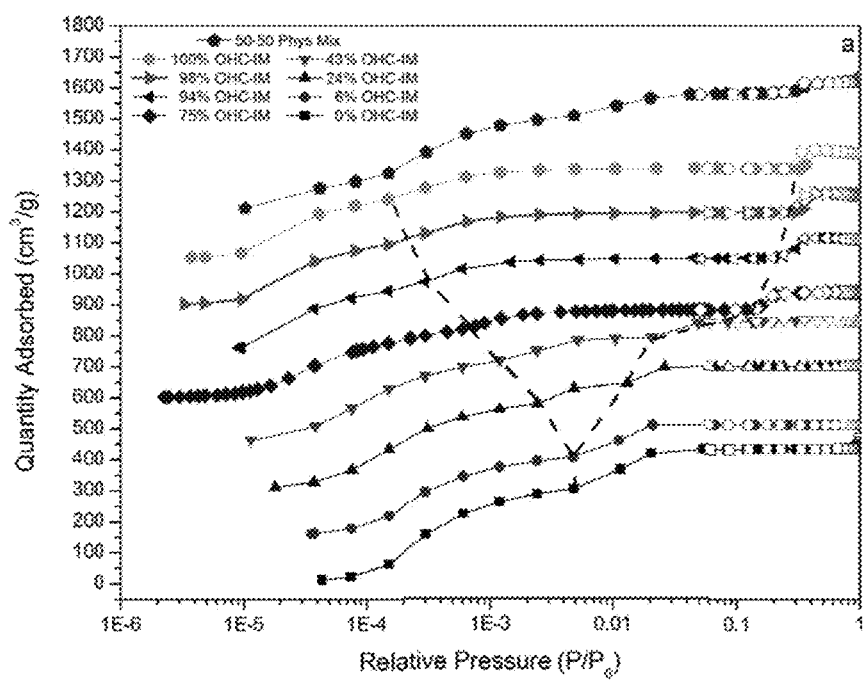
FIG. 6a illustrates nitrogen physisorption isotherms of ZIF-8-90, with isotherms stacked 150 $cm^3/g$ apart, in accordance with an embodiment of the disclosure.
Figure 6B:
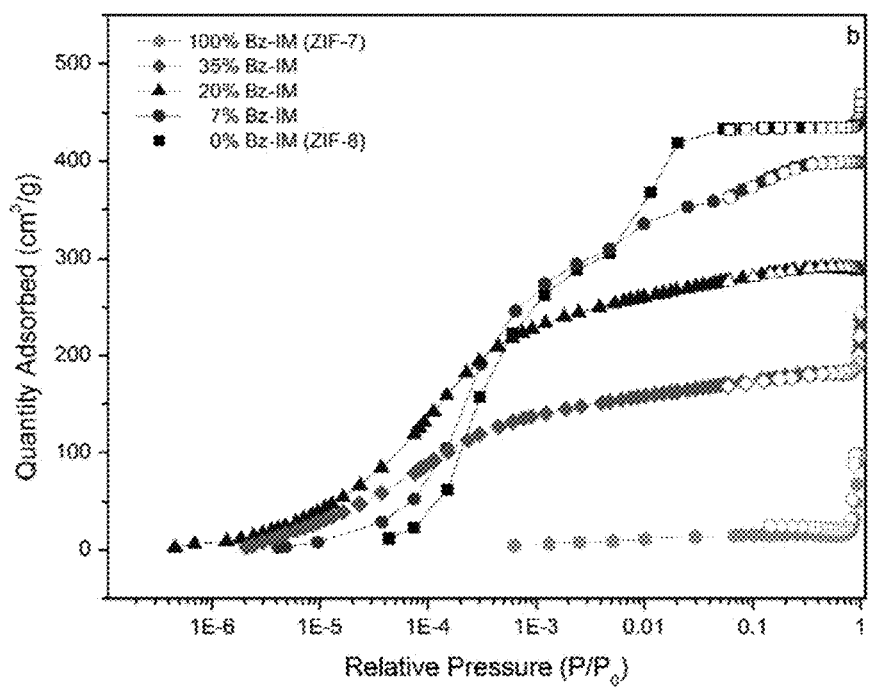
FIG. 6b illustrates nitrogen physisorption isotherms of ZIF-7-8 hybrids at different loadings of OHC-IM and Bz-IM, respectively, in accordance with an embodiment of the disclosure.

FIGS. 6a and 6b show nitrogen physisorption isotherms of ZIF-8-90 and ZIF-7-8 hybrids. Inclusion of either OHC-IM or Bz-IM reduces the maximum quantity adsorbed in comparison to pure ZIF-8, thus decreasing the micropore volume of the framework. It has been shown that ZIF-90 exhibits hysteresis at $P/P_0$~0.4, and this was attributed to a constriction in the micropores. As the OHC-IM loading increases in the framework, the single inflection point seen in ZIF-8 at $P/P_0$~$5\times10^{-3}$ (attributed to a gate-opening mechanism that allows more nitrogen into the micropores) turns into two inflection points as pure ZIF-90 is approached: one inflection still characteristic of the gate-opening effect at lower nitrogen activity (e.g., $P/P_0$~$10^{-4}$) and the other attributed to constriction in the micropores at higher nitrogen activity (e.g., $P/P_0$~0.4). To confirm that these inflection points and the isotherms are indeed a result of hybrid materials (containing a single phase with an essentially random dispersion of linkers in the framework), a 50-50 (molar) physical mixture of ZIF-8 and ZIF-90 crystals was prepared. As shown in FIG. 6a, the inflection points in the corresponding isotherm are characteristic of the parent framework materials and not of the hybrids at similar overall composition (e.g. 43% OHC-IM). This is a further indication that the materials prepared with our synthetic method are single phases with different microporosity from pure ZIF-8 or ZIF-90.

FIG. 6b shows physisorption isotherms of the ZIF-7-8 hybrids. As the Bz-IM loading increases, the micropore volume is severely reduced; for example, there is a 40% micropore volume reduction from pure ZIF-8 at only 20% Bz-IM loading. The inflection typical of ZIF-8 decreases and disappears as the loading increases. This indicates that the bulky Bz-IM linkers are much less amenable to rotational displacement. Thus, we hypothesize that inclusion of Bz-IM in the framework reduces and even eliminates gate-opening phenomena in the hybrid ZIF materials when probed with cryogenic nitrogen adsorption. In fact, the shape of the isotherm (Type I) with 20% Bz-IM loading is similar to the isotherm predicted for ZIF-8 by grand canonical Monte Carlo (GCMC) simulations that assume a rigid framework. The progressive suppression of the gate-opening phenomena in these hybrids provides a method for tuning the average pore size and the flexibility so that the material can be adapted to specific applications (separations, catalysis). Although ZIF-7 has been shown to admit condensable gases (e.g. $CO_2$, ethane) via a structural change, the pores are not accessible to nitrogen at 77 K, as shown in FIG. 6b.

Figure 7A:
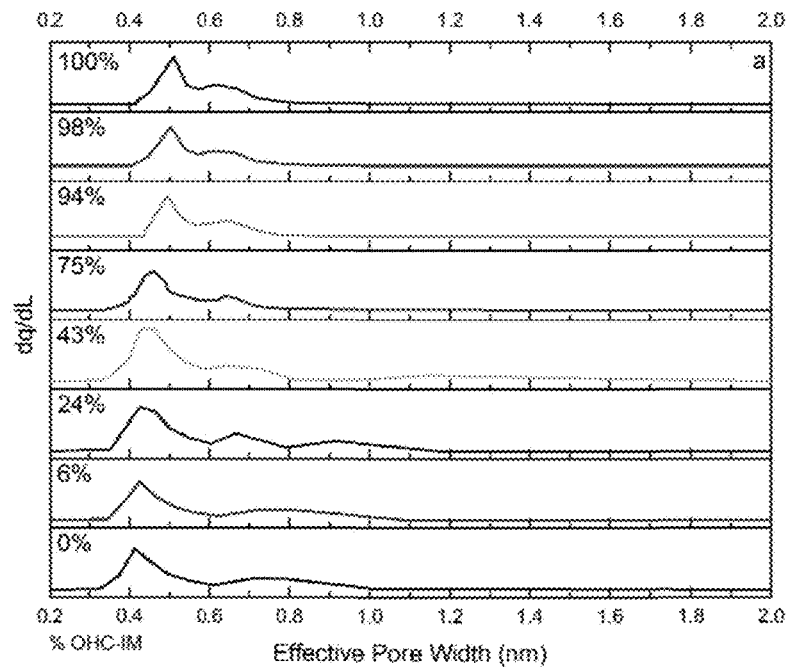
FIG. 7a illustrates pore size distributions determined by the HK method of ZIF-8-90 hybrids, in accordance with an embodiment of the disclosure.
Figure 7B:
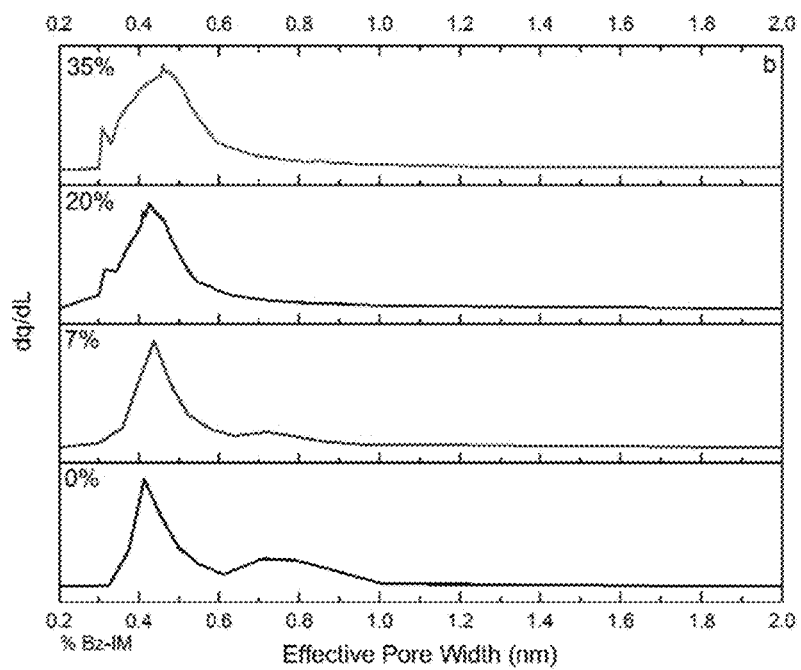
FIG. 7b illustrates pore size distributions determined by the HK method of ZIF-7-8 hybrids, in accordance with an embodiment of the disclosure.

Horváth-Kawazoe analysis was used to analyze the relative pore size distributions (PSDs) of the hybrid materials. It has been shown that some assumptions of these equations are not physically accurate and therefore do not provide correct absolute values of the PSDs. For example, the main pore size for both ZIF-8 and ZIF-90 predicted by the HK method are larger than the pore sizes determined crystallographically. However, the HK method can be reliably used for relative comparison of a series of structurally related materials. FIGS. 7a and 7b show the PSDs for both hybrid material types. ZIF-8 (0% OHC-IM) shows two pore size distributions, centered at ~0.4 nm and ~0.75 nm. The former represents the limiting pore diameter of the ZIF-8 windows. Considering the gate-opening mechanism, the latter PSD is interpreted as resulting from rotational displacement of linkers to allow further adsorption of nitrogen, and not due to an actual secondary pore system (e.g. the SOD cages) in the framework. This interpretation is supported by the fact that while the main pore size becomes larger with increasing OHC-IM loading (the pure ZIF-90 material shows a primary pore size of ~0.5 nm), the secondary PSD is quite different from the original ZIF-8 material and hence is unlikely to originate from a secondary pore system such as the ZIF cages, which maintain essentially the same dimensions in all the ZIF-8-90 hybrids. Interestingly, the gate-opening effect is still apparent in ZIF-90, an observation not shown or explained previously. This effect in ZIF-90 occurs at a significantly lower relative pressure ($P/P_0 \sim 10^{-4}$) than typically observed for ZIF-8 ($P/P_0 \sim 5 \times 10^{-3}$). Considering this difference, the gate-opening in ZIF-90 and in hybrids with higher OHC-IM loading can be interpreted as being more easily induced than in pure ZIF-8.

PSDs of the ZIF-7-8 hybrids are shown in FIG. 7b. As noted before, the isotherm inflection is related to the second PSD. At 7% Bz-IM loading, the intensity of the second PSD is reduced considerably, and it disappears at 20% Bz-IM. This indicates that Bz-IM groups block the rotational displacement of the imidazole linkers. The primary PSD shifts to overall smaller values, and at 20% Bz-IM, a PSD centered at ~0.32 nm appears. This shift to smaller pore sizes indicates that Bz-IM is effectively reducing the average pore size.

Example 2

Materials

Sodium formate (99%, $NaCO_2H$), 2-methylimidazole (98%, 2-MeIM), $Zn(NO_3)_2 \cdot 6H_2O$ (99%), 2-aminobenzimidazole (97%, 2-amBzIM), and carboxaldehyde-2-imidazole (99%, OHC-IM) were obtained from Alfa Aesar. Methanol (MeOH) and dimethylformamide (DMF) were obtained from BDH. Ethylenediamine (99%, en) was obtained from Sigma-Aldrich. All chemicals were used as received without further purification.

Synthesis of ZIF-8-ambz-(x).

A solution was prepared with (20-x) mmol 2-MeIM, x mmol 2-amBzIM, and 5 mmol $NaCO_2H$ in 50 mL deionized $H_2O$. The value x was varied between 0-10 to change the ratio of 2-MeIM:2-amBzIM in solution. To fully dissolve the 2-amBzIM, the solution was heated to 70° C. for at least 2 hrs in a round bottom flask until the solution turned clear. A separate solution containing 5 mmol $Zn(NO_3)_2 \cdot 6H_2O$ in 50 mL DMF was also prepared. After the imidazole solution cooled to room temperature, the Zn-salt solution was added and allowed to stir for 1 hr. The solution was then centrifuged at 10,000 rpm for 5 min and the precipitate was washed with MeOH. This washing was repeated three times, and then the precipitate was recovered by vacuum filtration and dried in an oven at 85° C. The yield of product was approximately 20-25% based on Zn.

Synthesis of ZIF-8-90-(50).

Synthesis of ZIF-8-90-(50) is a scaled-up reaction of a previously reported procedure. A solution was prepared containing 12.6 mmol OHC-IM, 87.4 mmol 2-MeIM, and 100 mmol of $NaCO_2H$ in 250 mL MeOH. To fully dissolve all the OHC-IM, this solution was heated to 50° C. in a sealed polyethylene bottle for 2 hrs. A separate solution was then prepared with 25 mmol $Zn(NO_3)_2 \cdot 6H_2O$ in 250 mL deionized $H_2O$. After the imidazole solution had cooled to room temperature, the Zn-salt solution was added and allowed to stir for 1 hr. The solution was centrifuged at 10,000 rpm for 5 min, and the precipitate was washed with MeOH after pouring off the supernatant. This was repeated again, and then the precipitate was recovered by vacuum filtration. The recovered product was dried in an oven at 85° C. The yield was approximately 20% based on Zn.

Functionalization of ZIF-8-90-(50).

The ZIF-8-90-(50) samples were functionalized with ethylenediamine to form ZIF-en samples. First, a dispersion of 0.2 g ZIF-8-90-(50) was prepared in 25 mL MeOH. Then, at room temperature, 1 mL ethylenediamine was added to the dispersion. Sealed in a Teflon cup, the ZIF dispersion was heated to 80° C. and stirred for 24 hrs. After cooling to room temperature, the powder was washed with MeOH and recovered by vacuum filtration. The powder sample turned from white to yellow after reaction.

Materials Characterization.

The ZIF materials were analyzed by powder X-ray diffraction (XRD) using an X'Pert Pro PANalytical X-ray Diffractometer. Diffraction measurements were done from 3.5-50° 2θ using an X'celerator detector. $N_2$ physisorption measurements were done on a Micromeritics ASAP 2020 surface area analyzer at −196° C. ZIF-8-ambz-(x) samples were degassed at 250° C. under vacuum for 18 hrs before physisorption analysis, whereas ZIF-8-90-(50) and ZIF-en samples were degassed at 150° C. under vacuum for 12 hrs. The BET surface area and t-plot micropore volume methods were used to analyze the relative surface properties of each sample. Fourier-transform infrared (FTIR) and Fourier-transform Raman (FT-Raman) spectroscopy were performed on ZIF-8-90-(50) and ZIF-en samples. The powder samples were prepared in KBr pellets for FTIR and then analyzed on a Bruker Vertex 80v FTIR Analyzer from 4000-400 $cm^{-1}$. For FT-Raman, powder samples were packed tightly in NMR tubes and analyzed on a Bruker RAM II FT-Raman Analyzer from 4000-400 cm$^{-1}$. To determine the linker composition in the framework, all samples were analyzed with solution $^1$H nuclear magnetic resonance (NMR) spectroscopy on a Mercury Vx 400 MHz spectrometer after digesting samples using d4-acetic acid (CD$_3$CO$_2$D). Solid state (SS) $^{13}$C cross polarization-magic angle spinning (CP-MAS) NMR was performed on a Bruker 300 MHz spectrometer, using a spinning rate of 10 kHz with a 4 mm rotor and collecting a minimum of 5,000 scans. ZIF decomposition stability was tested on a Netzsch STA-409-PG thermogravimetric analyzer (TGA). Powder samples were heated from room temperature to 900° C. with a ramp rate of 10° C./min in a diluted air stream (25% air/75% N$_2$).

Adsorption Measurements.

Adsorption measurements for CO$_2$ and CH$_4$ were carried out in a custom-built, constant-volume apparatus. Samples were tested at temperatures of 35, 55, and 75° C. to provide data at multiple temperatures, facilitating calculation of heats of adsorption for each gas and sample. Pressure ranges tested were typically from 0–1000 kPa. Samples were degassed at 100° C. under vacuum for at least 12 hrs before testing. Ultra-high purity CH$_4$ (99.999%) and bone-dry CO$_2$ (99.999%) were used in all adsorption measurements.

Adsorption Analysis.

Isotherms obtained from adsorption measurements were fit to a Toth isotherm to describe the heterogeneous surface resulting from the mixed-linker structure:

$$q_i = \frac{q_{sat} b_i p}{[1 + (b_i p)^{t_i}]^{1/t_i}} \quad (1)$$

where $q_i$ is the capacity for adsorbing component i at pressure, p, $q_{sat}$ is the saturation capacity, $b_i$ is the affinity constant of component i, and $t_i$ is the heterogeneity parameter. When $t_i$ is equal to 1, this equation becomes the Langmuir isotherm model. The change in the affinity constant, $b_i$, the heterogeneity parameter, $t_i$, and the saturation capacity, $q_{sat}$, with temperature can be described with the following $$b_i = b_{i,0} \exp\left[\frac{-\Delta H}{RT_0}\left(\frac{T_0}{T} - 1\right)\right] \quad (2)$$

$$t_i = t_0 + \alpha\left(1 - \frac{T_0}{T}\right) \quad (3)$$

$$q_{sat,i} = q_{sat,0} \exp\left[\chi\left(1 - \frac{T}{T_0}\right)\right] \quad (4)$$

where $b_{i,0}$ is the pre-exponential affinity constant, $-\Delta H_{ads}$ is the heat of adsorption at zero adsorbate loading, T is the absolute temperature, $T_0$ is the reference temperature (35° C.), $\alpha$ and $t_0$ are parameters used for thermal variation in the heterogeneity parameter, $t_i$, and $q_{sat,0}$ and $\chi$ represent changes in saturation capacity for each adsorbent. Isotherms at different temperatures for a single gas were fit to the Toth isotherm by maximizing the coefficient of determination (R$^2$) for all data simultaneously. The ZIF materials were analyzed with ideal adsorbed solution theory (IAST) assuming a gas mixture of 25% CO$_2$/75% CH$_4$. To perform the analysis, a thermodynamic criterion must be satisfied: the spreading pressures of each component are equal to each other ($\pi_i = \pi_j$), where $\pi$ is the spreading pressure calculated as:

$$\pi_i = \frac{RT}{A} \int_0^{p_i^0} \frac{q_i}{p} dp \quad (5)$$

Using Equation 1, the spreading pressure of component i can be expressed in terms of isotherm parameters:

$$\frac{\pi_i A}{RT} = \int_0^{p_i^0} \frac{q_{sat,i} b_i}{[1 + (b_i p)^{t_i}]^{1/t_i}} dp \quad (6)$$

Here, $p_i^0$ is obtained from the expression:

$$y_i p = x_i p_i^0 \quad (7)$$

where $y_i$ is the gas phase mole fraction, p is the absolute pressure, $x_i$ is the adsorbed phase mole fraction and $p_i^0$ is the gas-phase pressure corresponding to adsorbed-phase spreading pressure $\pi$, for the adsorption of pure component i. The adsorption selectivity ($\alpha_{1,2}$) for a specific gas pair can be calculated as:

$$\alpha_{1,2} = \frac{\left(\frac{x_1}{y_1}\right)}{\left(\frac{x_2}{y_2}\right)} \quad (8)$$

and the capacity at p and T can be calculated by $$\frac{1}{q} = \frac{x_1}{q(p_1^0)} + \frac{x_2}{q(p_2^0)} \quad (9)$$

and $$q_i = x_i q \quad (10)$$

To solve for $x_i$ and calculate selectivity and capacity, Equations 6-7 were solved iteratively.

ZIF-8-ambz-(x).

Figure 8A:
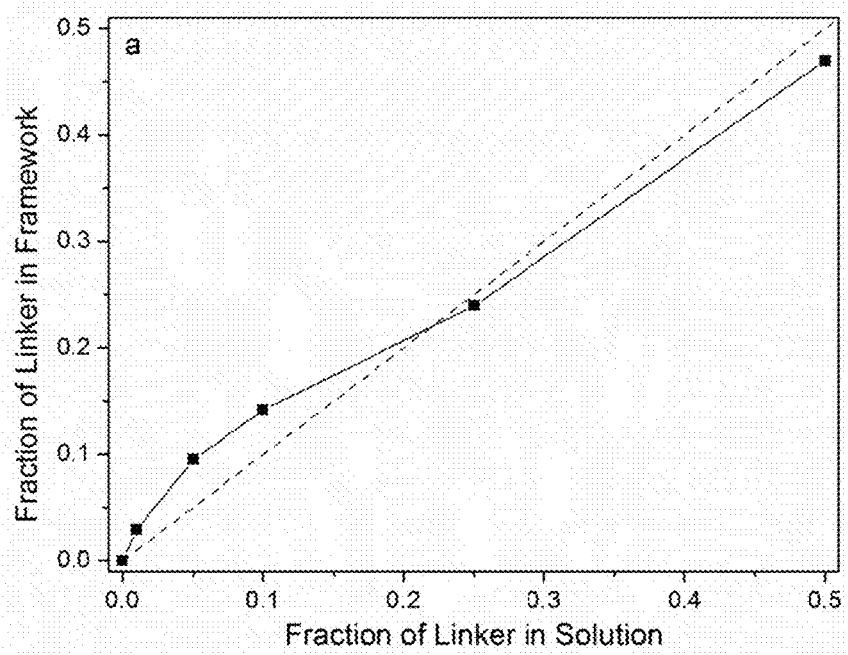
FIG. 8a illustrates $^1H$ NMR-based composition analysis of mixed-linker ZIFs prepared with 2-MeIM and 2-amBzIM linkers, in accordance with an embodiment of the disclosure.
Figure 8B:
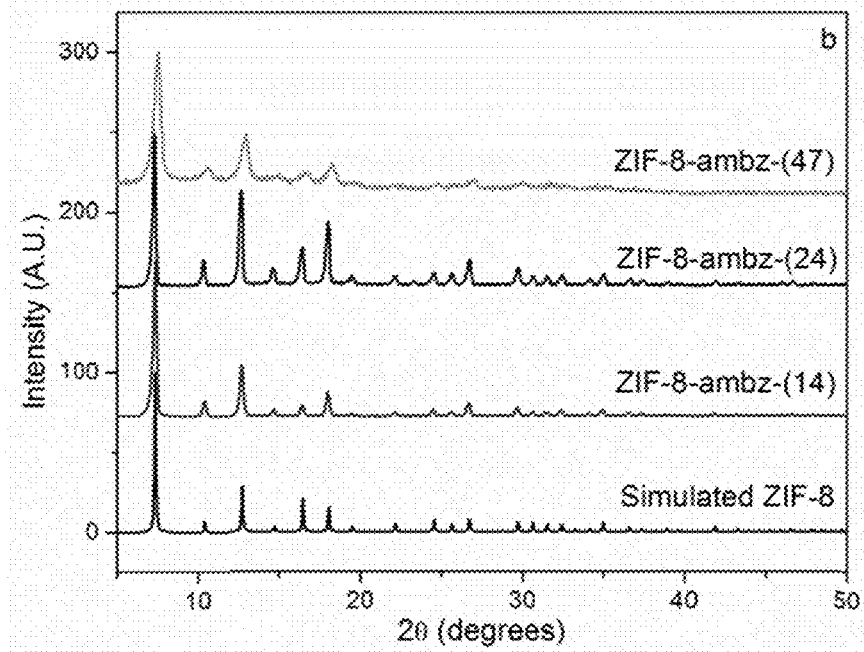
FIG. 8b illustrates powder XRD patterns of mixed-linker ZIFs prepared with 2-MeIM and ~2-amBzIM linkers, in accordance with an embodiment of the disclosure.

As our previous study on mixed-linker ZIFs showed that the inclusion of benzimidazole (Bz-IM) in a ZIF-8-like framework was difficult to control, a set of ZIF materials were prepared containing different proportions of 2-MeIM and 2-amBzIM linkers to understand if this substitution could be better controlled while maintaining a ZIF-8 crystal structure. FIG. 8a shows the fraction of 2-amBzIM linkers included in the framework obtained from $^1$H NMR spectra and derived from syntheses using up to 50% 2-amBzIM in the synthesis solution. In comparison to our previous study, we find that inclusion of 2-amBzIM is more controllable than Bz-IM. Because 2-amBzIM does not form any known single-linker ZIF structure, it is likely that formation of the ZIF-7 structure with Bz-IM is more thermodynamically favorable than any structure containing 2-amBzIM; therefore, the ZIFs obtained with 2-amBzIM represent a mixed-linker system with better control of linker composition while maintaining the cubic I-43m structure of ZIF-8. Powder XRD patterns (FIG. 8b) of the synthesized materials show that the I-43m crystal structure is maintained up to high substitution fractions of 2-amBzIM. At 47% 2-amBzIM in the framework, a significant peak broadening is observed in the XRD pattern. This is either due to the formation of a crystal with a disordered distribution of the two linkers, or due to a high degree of crystal strain arising from incorporation of the high fraction of 2-amBzIM in the ZIF crystal structure.

Figure 9:
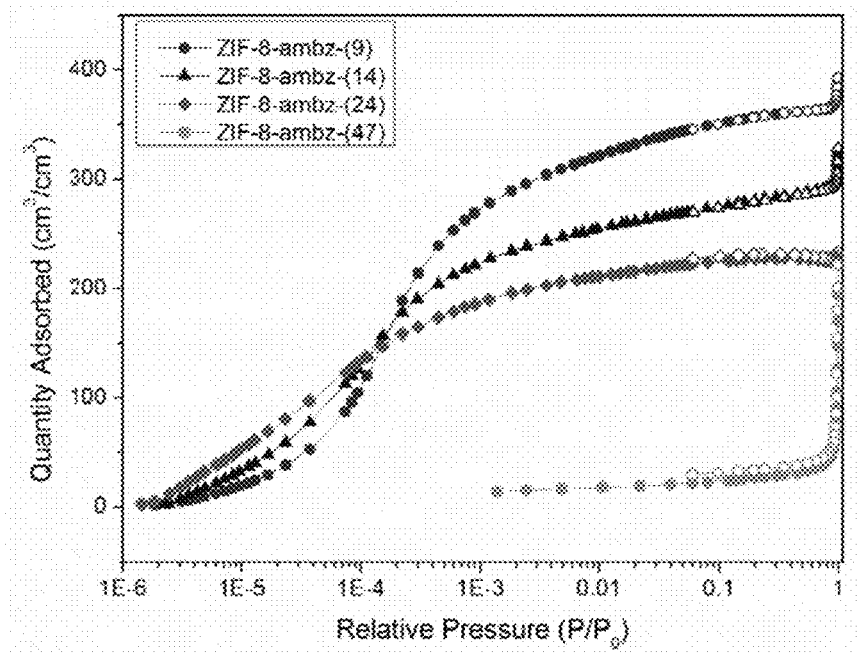
FIG. 9 illustrates $N_2$ physisorption isotherms of mixed-linker ZIFs with 2-amBzIM, in accordance with an embodiment of the disclosure.

Nitrogen physisorption was used to investigate the gate-opening properties of these mixed-linker ZIFs. FIG. 9 shows materials with modest loadings of 2-amBzIM (9.5% in the structure) show no evidence of gate-opening effects compared to ZIF-8. There is a reduction in micropore volume (see Table 1) with increasing linker substitution.

TABLE 1

Linker substitution, framework density, micropore volume and BET surface area of ZIF-8-ambz-(x), ZIF-8-90-(50), and ZIF-en materials.

| Sample | Linker Substitution (mol %)[a] | Framework Density (g/cm$^3$)[b] | t-plot micropore volume (cm$^3$/cm$^3$) | BET Surface Area (m$^2$/cm$^3$) |
|---|---|---|---|---|
| ZIF-8-ambz-(9) | 9.5 | 0.934 | 0.586 | 1640 |
| ZIF-8-ambz-(14) | 14 | 0.983 | 0.406 | 1160 |
| ZIF-8-ambz-(24) | 24 | 1.024 | 0.322 | 880 |
| ZIF-8-ambz-(47) | 47 | 1.120 | 0.014 | 70 |
| ZIF-8-90-(50) | 48 | 0.983 | 0.630 | 1670 |
| ZIF-en | 27[c] | 1.048 | 0.301 | 860 |

[a]Calculated from solution $^1$H NMR, balance is 2-MeIM
[b]Calculated from assuming no change in unit cell volume
[c]Total substitution = 22% en-IM + 5% OHC-IM Significantly, at 47% 2-amBzIM loading, there is complete loss of micropore volume and no uptake of $N_2$ at −196° C. To activate this material properly, the powder sample needed to be washed and soaked with MeOH at 50° C. for 24 hrs to remove occluded solvent molecules trapped in the pores during synthesis. If degassing at 250° C. was performed without this activation step, there was complete loss of crystallinity. When these samples were examined with TGA, the samples not soaked in MeOH showed mass loss before the material decomposed, whereas the samples soaked in MeOH showed no mass loss before decomposition. Based on the above observations, it is very likely that the higher 2-amBzIM substitution has significantly reduced the effective pore size and micropore volume of the ZIF material, blocking even small $N_2$ molecules from accessing the pores at −196° C.

$CO_2$ and $CH_4$ adsorption measurements were used to assess the changes in surface properties for the mixed-linker ZIFs containing 2-amBzIM, compared to ZIF-8. For comparison, the heats of adsorption at zero adsorbate loading for ZIF-8 are calculated to be −15.6 kJ/mol and −12.3 kJ/mol for $CO_2$ and $CH_4$, respectively (Table 2).

TABLE 2

Heats of adsorption for $CO_2$ and $CH_4$ obtained from Langmuir and Toth isotherm fits, Henry's law constants of ZIF materials and ideal selectivity of $CO_2$/$CH_4$.

| | −ΔH (kJ/mol) | | K (cm$^3$ (STP)/ cm$^3$ adsorbent)[b] | | |
|---|---|---|---|---|---|
| Sample | $CO_2$ | $CH_4$ | $CO_2$ | $CH_4$ | α (ideal) |
| ZIF-8[a] | 15.6 | 12.3 | 12.5 | 5.3 | 2.4 |
| ZIF-8-ambz-(14) | 19.4 | 12.5 | 19.3 | 7.0 | 2.8 |
| ZIF-8-ambz-(24) | 20.4 | 12.4 | 24.7 | 7.9 | 3.1 |
| ZIF-8-ambz-(47) | 22.1 | 15.6 | 14.1 | 4.0 | 3.5 |
| ZIF-8-90-(50) | 25.6 | 20.0 | 41.3 | 7.4 | 5.6 |
| ZIF-en | 33.9 | 26.2 | 103 | 7.9 | 13.1 |

[a]Values for ZIF-8 are taken from Refs. 7, 9, 31
[b]Henry's constants were predicted by ($q_{sat}$ · b)

Figure 10A:
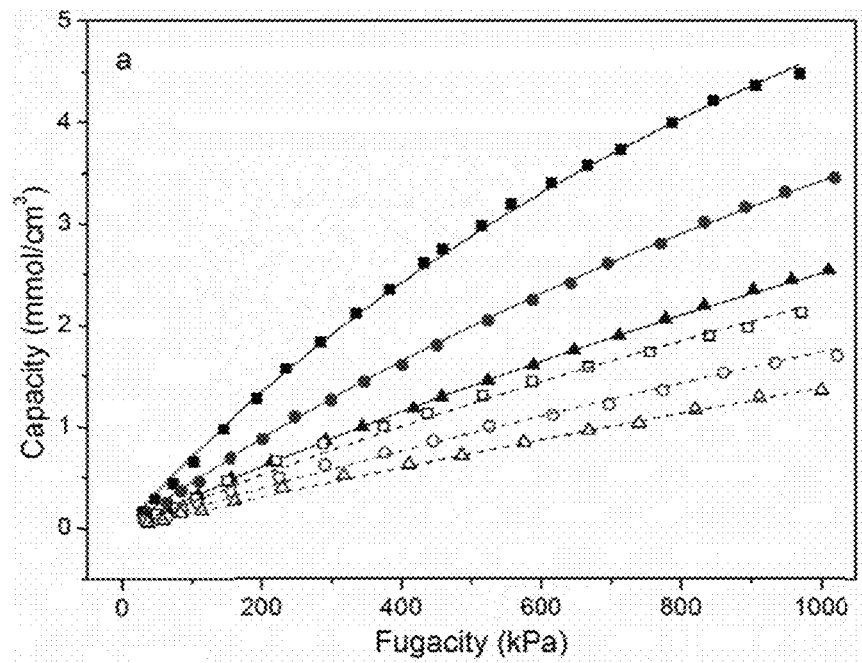
FIG. 10a illustrates $CO_2$ and $CH_4$ adsorption isotherms ZIF-8-ambz-(14), in accordance with an embodiment of the disclosure.

Framework densities were calculated assuming no change in the unit cell volume of ZIF-8, and these values are shown in Table 1 for each sample presented. FIG. 10a shows the $CO_2$ and $CH_4$ adsorption data and fits of the Toth isotherm for the ZIF-8-ambz-(14) material. Open symbols denote $CH_4$ adsorption, closed symbols $CO_2$. Squares: T=35° C.; circles: T=55° C.; triangles: T=75° C. The capacities reported in this figure are presented in units of mmol/cm$^3$, instead of the more typical mmol/g. Because the mass adsorption capacity of MOFs can often be misleading due to low bulk or framework densities, the adsorption units used here reflect the material capacity and performance more accurately. When comparing the initial slope of the adsorption isotherms of the ZIF-8-ambz-(14) material to those of ZIF-8, it is clear that there is not much change in the affinity for $CO_2$ or $CH_4$ at this substitution level of 2-amBzIM. Although the substituting linker contains a primary amine functional group, the basicity of this amine is greatly affected by the fused aromatic ring of the imidazolate and benzyl groups. From the isotherm fit, the heats of adsorption were found to be −19.4 kJ/mol and −12.5 kJ/mol for $CO_2$ and $CH_4$, respectively. The heat of adsorption for $CH_4$ is almost identical with that of ZIF-8. It has been shown by both simulations and neutron scattering measurements that $CH_4$ adsorbs in the 6-membered ring (MR) of ZIF-8 at lower pressures, interacting directly with the C=C bond on the 2-MeIM linker. Because 2-amBzIM has similar adsorption sites, it is not surprising that no change in the heat of adsorption of $CH_4$ was seen in ZIF-8-ambz-(x) materials compared with ZIF-8. An increase of about 4 kJ/mol in the heat of adsorption for $CO_2$ in the ZIF-8-ambz-(x) material relative to ZIF-8 is also consistent with the introduction of a more polar functional group than the methyl group on the ZIF-8 linker; however, this does not greatly affect the overall affinity for $CO_2$ in this sample.

Figure 10B:
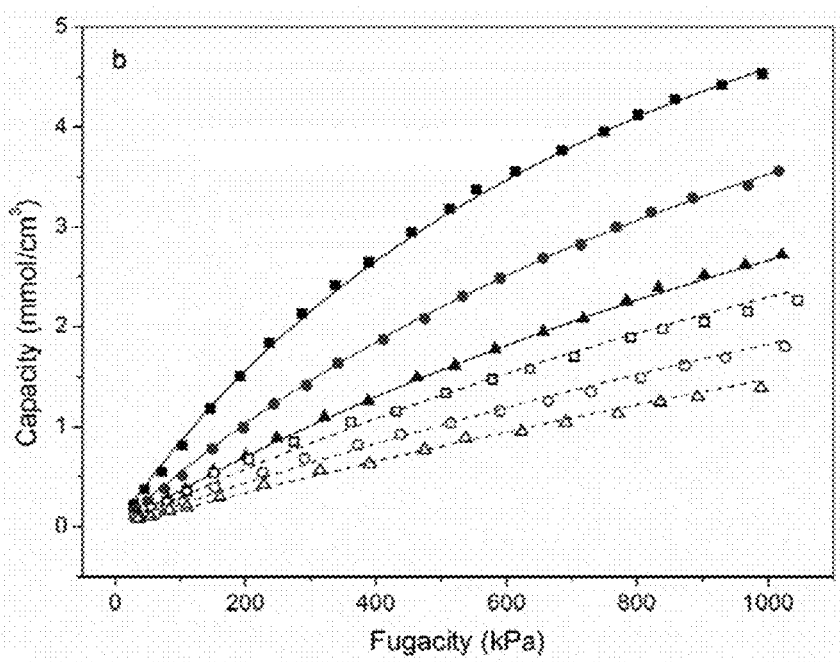
FIG. 10b illustrates $CO_2$ and $CH_4$ adsorption isotherms for ZIF-8-ambz-(24), in accordance with an embodiment of the disclosure.
Figure 10C:
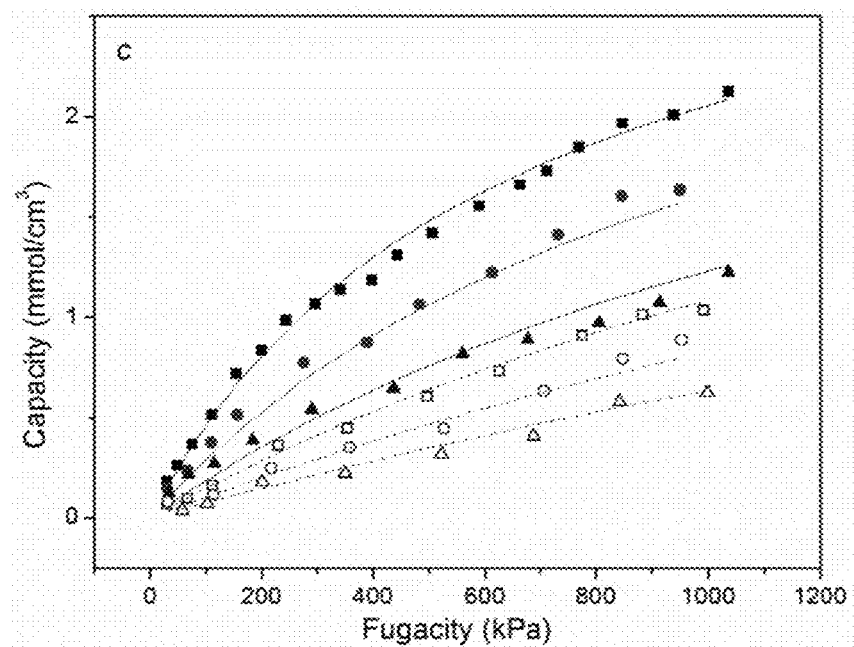
FIG. 10c illustrates $CO_2$ and $CH_4$ adsorption isotherms (c) ZIF-8-ambz-47, in accordance with an embodiment of the disclosure.

As FIGS. 10b and 10c show, with increasing substitution of 2-amBzIM in the ZIF framework, there is an overall increase in the affinity for $CO_2$ without much change in the affinity for $CH_4$. There is a concomitant increase in the heat of adsorption for $CO_2$. Table 2 summarizes the heats of adsorption obtained for each material. With increasing fraction of 2-amBzIM, the heats of $CO_2$ adsorption show a monotonic increase, consistent with the increasing binding energy due to the polar functional groups. Although ZIF-8-ambz-(14) and ZIF-8-ambz-(24) showed excellent fits to a Langmuir isotherm ($t_i$=1), the Toth isotherm provided the best overall fit for the ZIF-8-ambz-(47) material. It is likely that the high substitution obtained in this sample causes significant heterogeneity in the internal surface of the ZIF. Interestingly, although $N_2$ physisorption showed complete loss of micropore volume at −196° C., ZIF-8-ambz-(47) adsorbed both $CO_2$ and $CH_4$ at ambient temperatures. This shows these materials can have significant 'breathing' and 'flexibility' effects that allow molecular adsorption and diffusion even when containing bulky benzimidazolate-type linkers. Although no gate-opening phenomena is observed from $N_2$ physisorption, there is clearly some freedom for the linkers to rotate or vibrate to allow adsorption of larger molecules at ambient temperatures, similar to behavior observed in ZIF-8. Table 2 shows the Henry's constants obtained from isotherm fits and the ideal selectivity, as well as data from ZIF-8 as a standard to compare the $CO_2/CH_4$ selectivity. Because there is significant reduction in the total adsorption capacity in the ZIF-8-ambz-(47) sample, the Henry's constant decreases, but there is an overall increase in selectivity as the 2-amBzIM fraction increases. Considering that these materials also have a shrinking pore size with increasing 2-amBzIM fraction, it is likely the overall transport selectivity of these materials is higher than that of ZIF-8 and hence the materials can be useful for membrane-based $CO_2$ separations.

Postsynthetic Modification of ZIF-8-90-(50).

Figure 11:
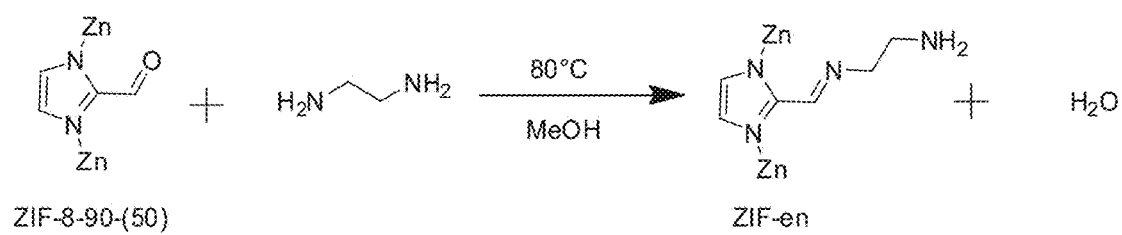
FIG. 11 illustrates the strategy for producing a ZIF material with a primary amine far enough removed from the aromatic ring of the organic linker to have useful basicity, in accordance with an embodiment of the disclosure.
Figure 12A:
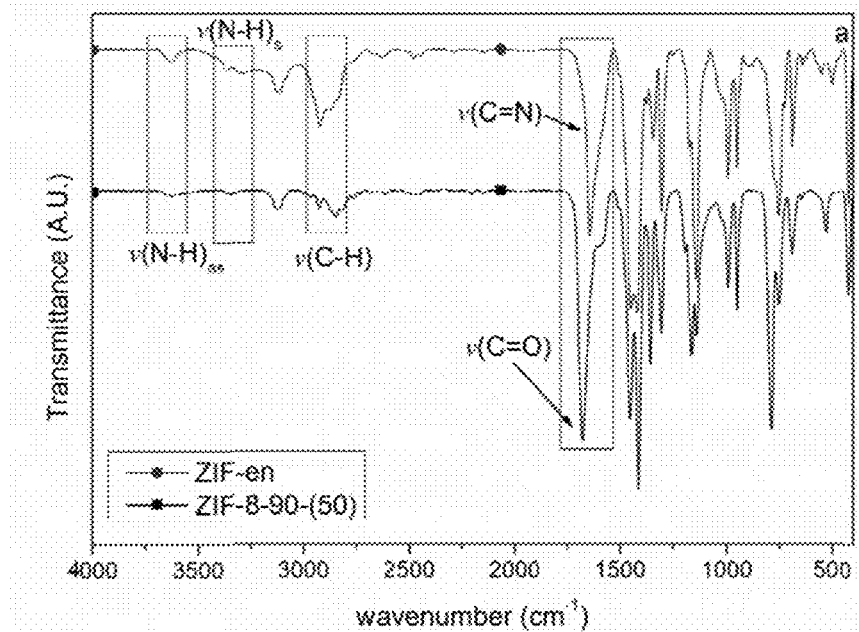
FIG. 12a illustrates FTIR spectra of ZIF-8-90-(50) (squares) and ZIF-en (circles), in accordance with an embodiment of the disclosure.
Figure 12B:
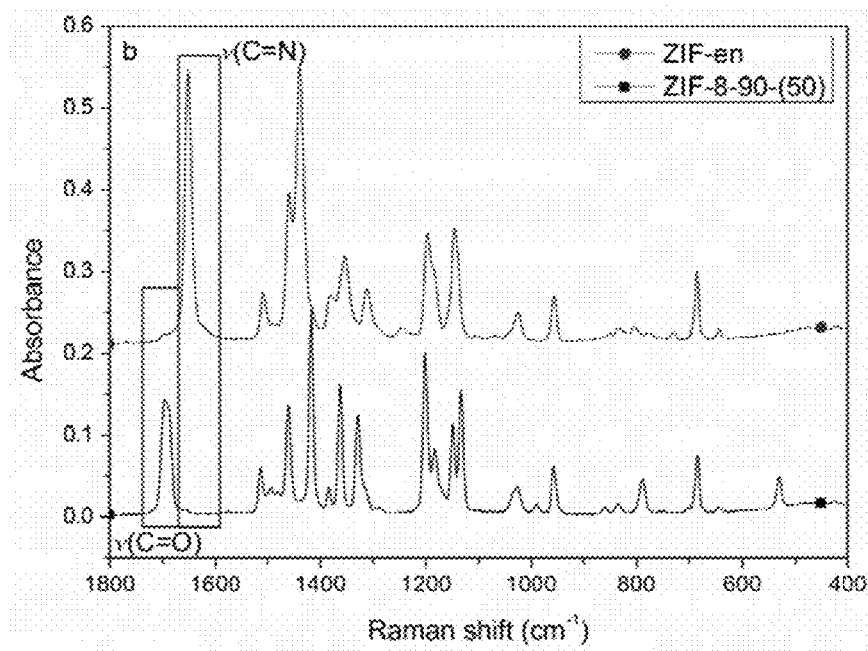
FIG. 12b illustrates FT-Raman spectra of ZIF-8-90-(50) (squares) and ZIF-en (circles), in accordance with an embodiment of the disclosure.

The previous PSM attempts on ZIF materials showed a detrimental loss of micropore volume after functionalization. We hypothesized that the present mixed-linker synthetic strategy that allows control over the amount of reactive sites can be able to prevent a total loss of pore volume while still providing active sites for functionalization. FIG. 11 shows the strategy for producing a ZIF material with a primary amine far enough removed from the aromatic ring of the organic linker to have useful basicity. FIGS. 12 a-b show FTIR and FT-Raman spectra of ZIF-8-90-(50) and the modified material ZIF-en. Several FTIR bands that show significant changes are highlighted in FIG. 12a. Although the bands in the N—H stretching region (3600-3200 $cm^{-1}$) are broad, there is an appearance of two symmetric bands and one asymmetric band after functionalization, indicating the —$NH_2$ moiety in ZIF-en. In the carbonyl region (1700-1600 $cm^{-1}$), there is a disappearance of the band from the aldehyde and an appearance of a band in the imine region, suggesting that the aldehyde is converted to an imine by reacting with ethylenediamine; however, there can be an appearance of —N—H bending in the same region, making it necessary to also examine the FT-Raman spectra of ZIF-en. FT-Raman spectra (FIG. 12b) confirm the disappearance of the $v(C=O)$ at 1700 $cm^{-1}$ and the appearance of the $v(C=N)$ band at 1650 $cm^{-1}$; however, a weaker $v(C=O)$ band is still present in ZIF-en, indicating that not all carbonyl groups were reacted.

Figure 13A:
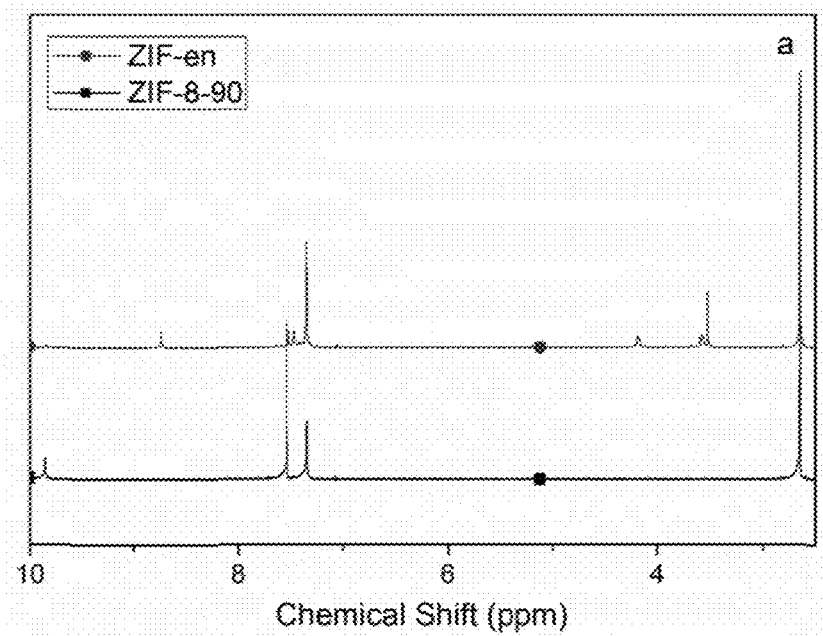
FIG. 13a illustrates solution $^1H$ NMR of ZIF-8-90-(50) (squares) and ZIF-en (circles), in accordance with an embodiment of the disclosure.
Figure 13B:
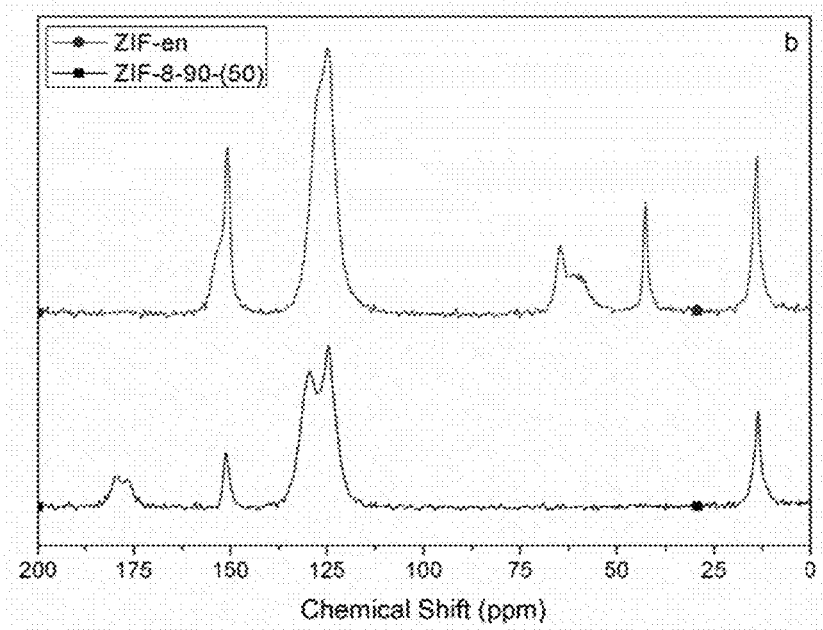
FIG. 13b illustrates $SS^{13}C$ CP-MAS NMR spectra of ZIF-8-90-(50) (squares) and ZIF-en (circles), in accordance with an embodiment of the disclosure.

NMR spectroscopy was used to identify the functional groups in the ZIF framework and also to determine if there is any 'cross-linking' caused by reaction of —$NH_2$ groups of ethylenediamine with nearby OHC-IM linkers. Solution $^1H$ NMR spectra of the deuterated acid-digested ZIF materials are shown in FIG. 13a. The chemical shift associated with the aldehyde ($\delta$ ~9.9 ppm) nearly disappears after PSM, and there is an appearance of a peak associated with an imine bonded to an aromatic ring ($\delta$ ~8.5 ppm). Taken together, these chemical shifts show a combined linker substitution of 27% (5% aldehyde and 22% en) after functionalization compared with 48% substitution prior to functionalization. This indicates 46% loss of total OHC-IM linker during PSM, with 81% of the remaining OHC-IM linkers in ZIF-en converted to the functionalized amine linker. However, the TGA mass loss curves of these materials show no significant changes in the total inorganic content (Zn). This indicates that there is some overall loss of ZIF particles during functionalization, but not the selective etching of a linker. It should also be noted that the overall yield of ZIF following functionalization was approximately 60% of the starting ZIF mass. Therefore, the change in the relative fractions of the different linkers in ZIF-en, compared to ZIF-8-90-(50), is best explained as being due to some dissolution of the ZIF material during PSM. The linkers dissolved in solution can then undergo PSE with the ZIF material, changing the overall linker ratios in the final material. It has already been shown that ZIF materials can easily dissolve in certain solvents and even recrystallize upon cooling. When the integrated area of the imine chemical shift ($\delta$ ~8.5 ppm) was compared to the methylene group ($\delta$ ~4.2, 3.5 ppm), we found a ratio of 1:2, suggesting no cross-linking of OHC-IM linkers by ethylenediamine molecules. In the case of $SS^{13}C$ CP-MAS NMR spectra (FIG. 13b), there was no appearance of an aldehyde peak in the region of $\delta$ ~170-180 ppm following functionalization likely due to low concentration in the framework. Two methylene (—$CH_2$) peaks appear at $\delta$ ~55-70 ppm and 42 ppm and can be associated with the ethyl linker between the imine and amine functional groups in ZIF-en. Previously, the peak associated with imine formation in ZIF-90 was attributed to a chemical shift of 60 ppm, meaning the broad peak at $\delta$ ~55-70 ppm is the methylene —$CH_2$ bonded to imine nitrogen. Therefore, the other peak at 42 ppm is a resonance of the methylene —$CH_2$ bonded to the primary amine nitrogen group. The shoulder at 150 ppm is likely associated with C=N bond formation from the imine. Overall, the NMR spectra suggest a high conversion of the aldehyde groups of ZIF-8-90-(50) to imine groups in ZIF-en, and there is no evidence of cross-linking of nearby linkers by ethylenediamine.

Figure 14A:
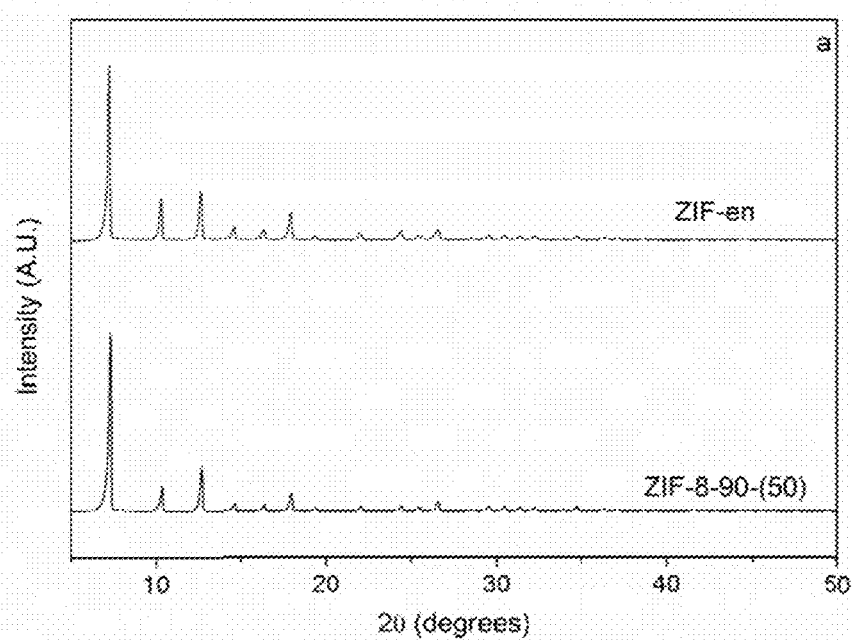
FIG. 14a illustrates powder XRD patterns of ZIF-8-90-(50) and ZIF-en showing maintenance of crystal structure after functionalization, in accordance with an embodiment of the disclosure.
Figure 14B:
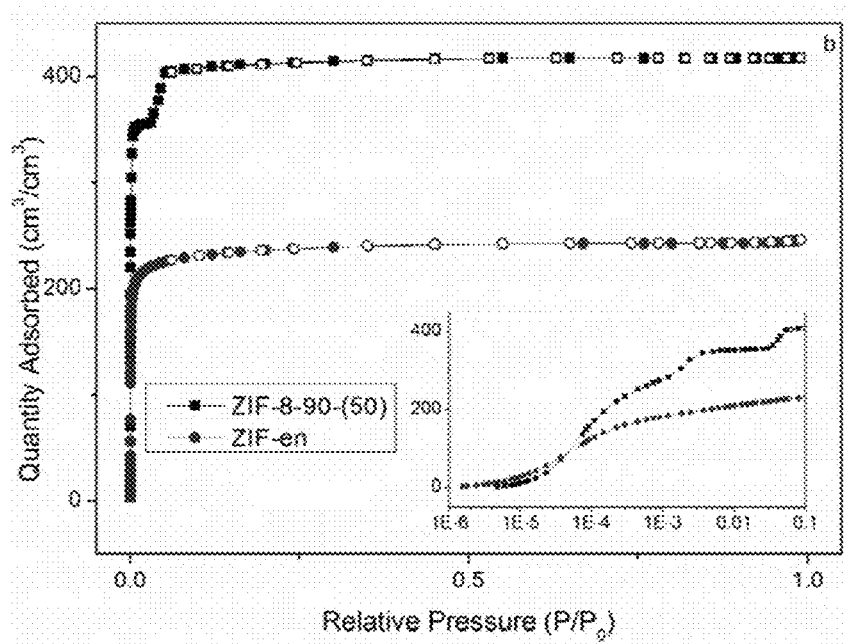
FIG. 14b illustrates $N_2$ physisorption isotherms of ZIF-8-90-(50) and ZIF-en, in accordance with an embodiment of the disclosure.

Although there are changes in the relative fractions of the two linkers following PSM, both powder XRD and $N_2$ physisorption show excellent preservation of the ZIF crystal structure and significant retention of micropore volume (FIGS. 14 a-b). From t-plot micropore volume calculations, a loss of 52% of the pore volume was observed after functionalizing the ZIF material. Considering that previous efforts to functionalize the internal carbonyl groups of ZIF-90 led to near-complete loss of micropore volume, our characterization results are encouraging. They indicate that ZIF-en still allows gas diffusion through the pores, and has good adsorption properties—both of which make it potentially useful for gas separation applications.

Figure 15A:
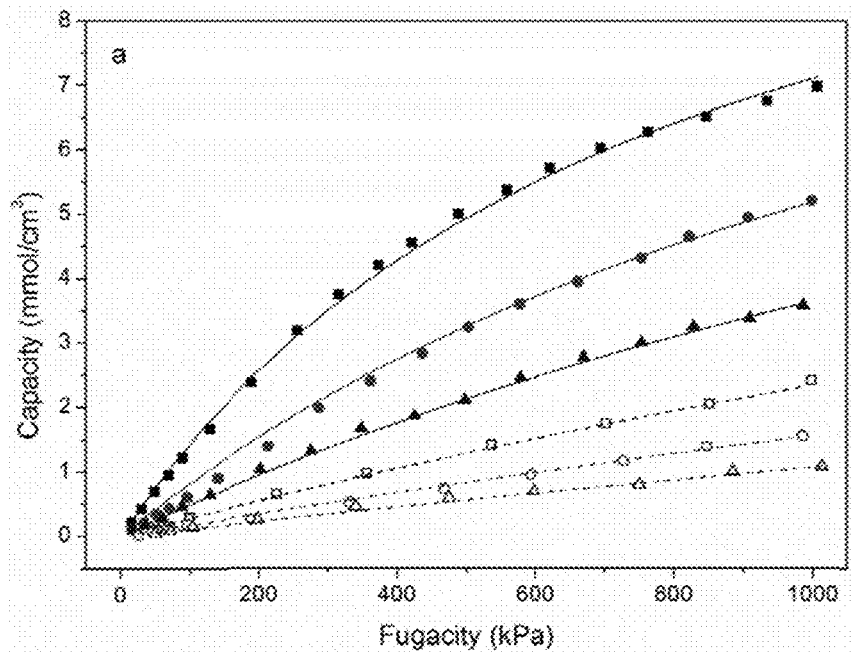
FIG. 15a illustrates $CO_2$ and $CH_4$ adsorption isotherms of ZIF-8-90-(50), in accordance with an embodiment of the disclosure.
Figure 15B:
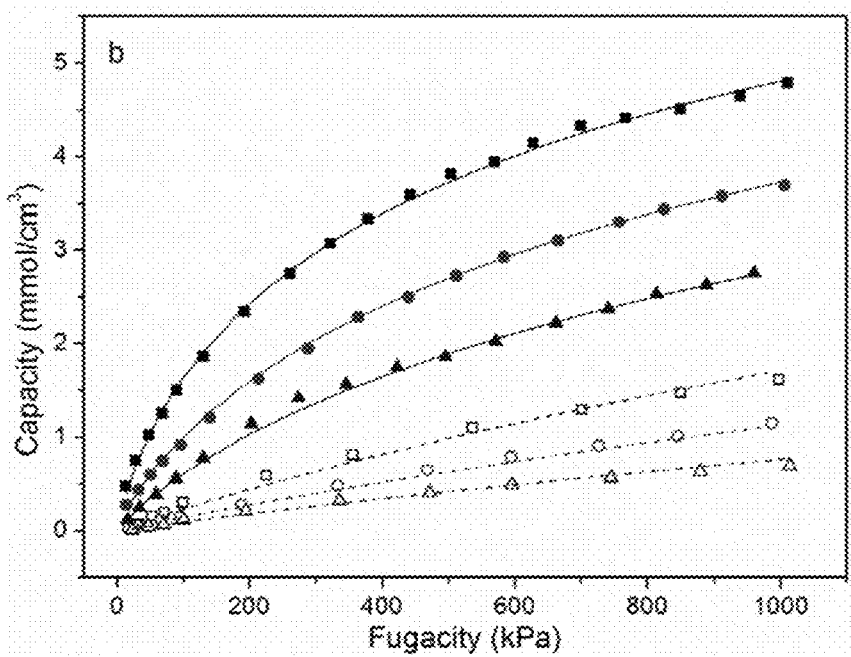
FIG. 15b illustrates $CO_2$ and $CH_4$ adsorption isotherms of ZIF-en, in accordance with an embodiment of the disclosure.

FIGS. 15a and 15b show $CO_2$ and $CH_4$ adsorption properties of ZIF-8-90-(50) and ZIF-en, respectively. Open symbols denote $CH_4$ adsorption, closed symbols $CO_2$. Squares: T=35° C.; circles: T=55° C.; triangles: T=75° C. As seen in Table 2, the heats of adsorption for both $CO_2$ and $CH_4$ increased after PSM of ZIF-8-90-(50). The heat of adsorption values obtained for ZIF-en are close to typical values for the commercial $CO_2$ adsorbent zeolite 13X; however, the affinity constants for ZIF-en are much lower than 13X (Table S1). Unlike zeolite 13X, ZIF-en likely does not have high affinity for $H_2O$, which significantly affects separation performance in 13X. There is significant enhancement of $CO_2$ affinity for ZIF-en when compared to ZIF-8-90-(50) or previously published data on ZIF-8. In addition, even though there is a 52% reduction in micropore volume in ZIF-en, the $CO_2$ capacity does not decrease greatly. When comparing the Henry's law constants of ZIF-8-90-(50) and ZIF-en, the ideal selectivity is found to increase from 6 to 13 after PSM, the latter being nearly 6 times higher than that of BPL carbon. Overall, we conclude that the functionalization of ZIF-8-90-(50) with ethylenediamine leads to a promising enhancement of $CO_2/CH_4$ selectivity.

IAST Predictions.

Figure 16A:
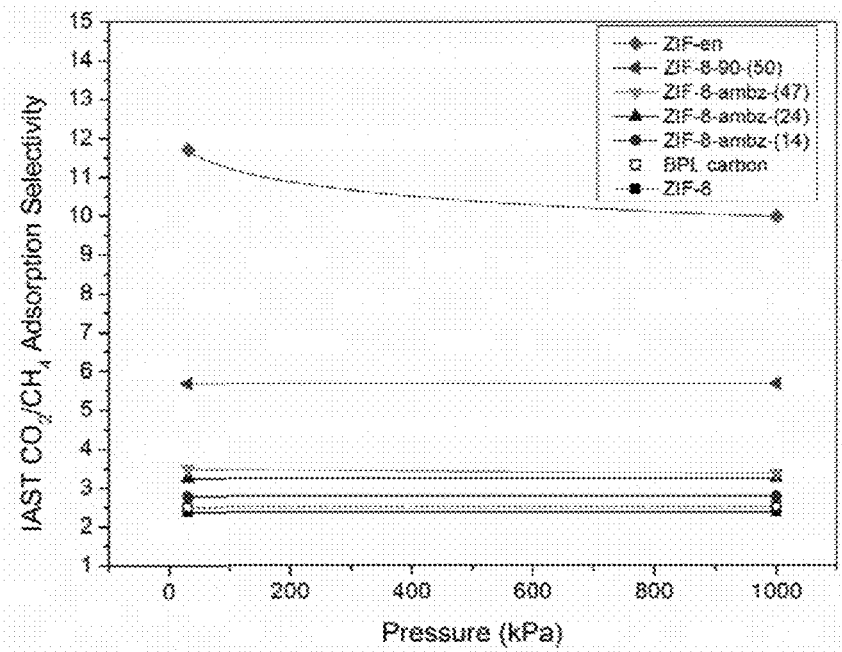
FIG. 16a-b illustrate LAST calculations of the selective $CO_2$ adsorption performance of ZIF materials assuming 25% $CO_2$/75% $CH_4$ gas phase mixture, in accordance with an embodiment of the disclosure.
Figure 16B:
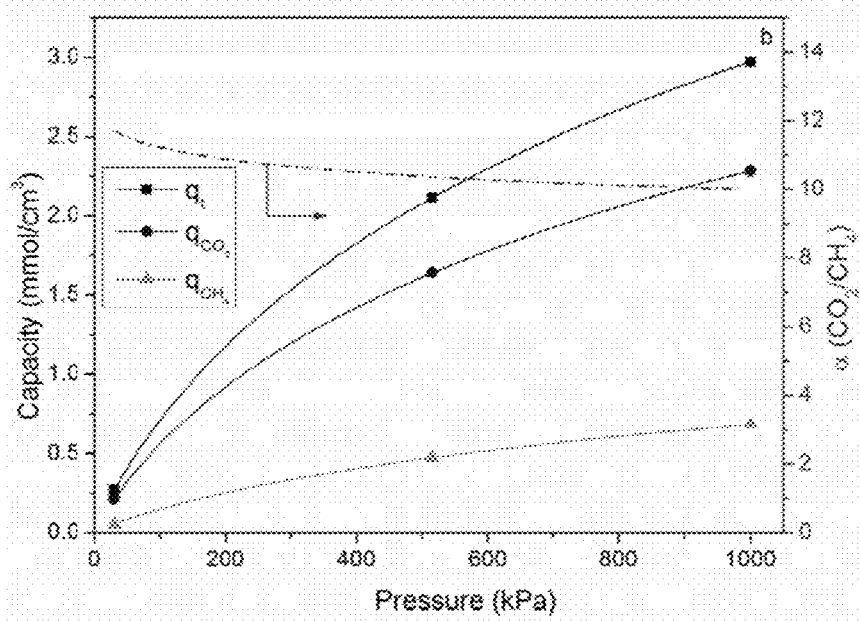

The IAST is useful for assessing an adsorbent's performance in multicomponent systems. FIG. 16a shows the adsorption selectivity from IAST calculations for the adsorbents considered in this study. The single-component adsorption parameters required for the IAST predictions are obtained from our experimental data. Although our mixed-linker ZIFs can have heterogeneous surfaces, thereby potentially decreasing the accuracy of IAST predictions, it is still useful as a tool for initial assessment of adsorption characteristics. Additionally, it has been shown that if the chosen single-component adsorption model fits the experimental data well, then IAST provides good predictions of mixed gas adsorption. Overall, the materials studied here show improvement over ZIF-8 and BPL carbon for $CO_2/CH_4$ selectivity. Considering the difficulty and expensive linkers required to make ZIFs with selectivities comparable to ZIF-en (e.g., ZIF-78), it can be more prudent to alter ZIF adsorption and gas separation properties by a mixed-linker and/or PSM route rather than using more expensive linkers if the materials are to be considered for practical replacements of commercially available materials (BPL carbon). Interestingly, ZIF-en shows an asymptotic behavior for selectivity at low pressures. The mixed gas adsorption capacity for this sample is shown in FIG. 16b. Like other amine-modified adsorbents, ZIF-en can have high heats of adsorption (and thus selectivity) at low partial pressures of $CO_2$.

The invention claimed is:

1. A metal-organic framework (MOF) comprising:
a hybrid zeolitic imidazolate framework comprising:
   a first imidazolate;
   a second imidazolate; and
   a metal ion;
wherein the first imidazolate comprises 2-methylimidazolate and the second imidazolate comprises carboxaldehyde-2-imidazolate, or the first imidazolate comprises benzimidazolate and the second imidazolate comprises 2-aminobenzimidazolate, or the first imidazolate comprises 2-methylimidazolate and the second imidazolate comprises imidazolate.

2. The MOF of claim 1, wherein the first imidazolate comprises benzimidazolate and the second imidazolate comprises 2-aminobenzimidazolate.

3. The MOF of claim 1, wherein the first imidazolate comprises 2-methylimidazolate and the second imidazolate comprises imidazolate.

4. The MOF of claim 1, wherein the metal ion is a transition metal.

5. The MOF of claim 1, wherein the metal ion is zinc.

6. The MOF of claim 1, wherein the metal ion is cobalt.

7. The MOF of claim 1, wherein the hybrid ZIF has $CO_2/CH_4$ selectivity of at least 1.2 times greater than a non-hybrid ZIF.

8. The MOF of claim 1, wherein the hybrid ZIF has $CO_2/CH_4$ adsorption selectivity from about 2.5 to about 13.1.

9. The MOF of claim 1, wherein the hybrid ZIF has a pore size from about 0.25 to about 0.40 nm.

10. The MOF of claim 1, wherein the hybrid ZIF has a continuous crystal structure.

11. A metal-organic framework (MOF) comprising:
a hybrid zeolitic imidazolate framework comprising:
   a first imidazolate;
   a second imidazolate; and
   a metal ion;
the MOF further comprising a functionalized hybrid ZIF.

12. The MOF of claim 11, wherein the functionalized hybrid ZIF comprises an aldehyde.

13. The MOF of claim 11, wherein the functionalized hybrid ZIF comprises an amine.

14. A molecular sieve device comprising a metal-organic framework (MOF) comprising:
a hybrid zeolitic imidazolate framework comprising:
   a first imidazolate;
   a second imidazolate; and
   a metal ion;
   wherein the hybrid ZIF has a pore size from about 0.25 to about 0.40 nm.

15. The device of claim 14, wherein the hybrid ZIF has $CO_2/CH_4$ selectivity of at least 1.2 times greater than a non-hybrid ZIF.

16. The device of claim 14, wherein the hybrid ZIF has $CO_2/CH_4$ adsorption selectivity from about 2.5 to about 13.1.

17. The MOF of claim 1, wherein the first imidazolate comprises 2-methylimidazolate and the second imidazolate comprises carboxaldehyde-2-imidazolate.

* * * * *